(12) United States Patent
Melkonyan et al.

(10) Patent No.: US 9,163,229 B2
(45) Date of Patent: Oct. 20, 2015

(54) COMPOSITIONS, METHODS AND KITS FOR ISOLATING NUCLEIC ACIDS FROM BODY FLUIDS USING ANION EXCHANGE MEDIA

(75) Inventors: Hovsep Melkonyan, Princeton, NJ (US); Erik Meyer, Princeton, NJ (US); William John Feaver, East Brunswick, NJ (US); Samuil R. Umansky, Princeton, NJ (US)

(73) Assignee: Trovagene, Inc., San Diego, CA (US)

( * ) Notice: Subject to any disclaimer, the term of this patent is extended or adjusted under 35 U.S.C. 154(b) by 273 days.

(21) Appl. No.: 11/974,016

(22) Filed: Oct. 10, 2007

(65) Prior Publication Data

US 2008/0139801 A1    Jun. 12, 2008

Related U.S. Application Data

(60) Provisional application No. 60/850,839, filed on Oct. 10, 2006.

(51) Int. Cl.
| | | |
|---|---|---|
| *C07H 21/02* | (2006.01) | |
| *C07H 21/04* | (2006.01) | |
| *C12N 15/10* | (2006.01) | |
| *C12Q 1/68* | (2006.01) | |

(52) U.S. Cl.
CPC .......... *C12N 15/101* (2013.01); *C12N 15/1006* (2013.01); *C12N 15/1017* (2013.01)

(58) Field of Classification Search
CPC .................................................... C12N 15/101
See application file for complete search history.

(56) References Cited

U.S. PATENT DOCUMENTS

| | | | |
|---|---|---|---|
| 4,683,195 A | 7/1987 | Mullis et al. ...................... 435/6 |
| 4,683,202 A | 7/1987 | Mullis ........................... 435/91.2 |
| 4,935,342 A | 6/1990 | Seligson et al. .................. 435/6 |
| 5,139,742 A | 8/1992 | Heijink ........................... 422/58 |
| 5,660,984 A * | 8/1997 | Davis et al. ....................... 435/6 |
| 5,990,301 A | 11/1999 | Colpan et al. |
| 6,492,144 B1 | 12/2002 | Umansky et al. |
| 6,872,527 B2 | 3/2005 | Gerdes et al. .................... 435/6 |

FOREIGN PATENT DOCUMENTS

| | | |
|---|---|---|
| EP | 0270017 A2 | 6/1988 |
| EP | 0 268 946 | 9/1993 |
| WO | WO 95/01359 | 1/1995 |
| WO | WO-0070041 A1 | 11/2000 |
| WO | WO-2008039669 A1 | 4/2008 |

OTHER PUBLICATIONS

Chen, S-H. et al., J. Chromatogr. B, vol. 692, pp. 43-51 (1997).*
Al-Yatama et al., 2001; Prenat Diagn, 21:399-402.
Lichstenstein, et al., 2001; Ann NY Acad Sci, 945:239-249.
Umansky, et al., 2006; Expert Rev. Mol. Diagn., 6:153-163.
Umansky, et al., 1982; Biochim. Biophys. Acta, 655:9-17.
Utting, et al., 2002; Clin Cancer Res, 8:35-40.
Yamakawa et al., 1996; Analytical Biochemistry, 24:242-250.
International Search Report for PCT/US07/21723, mailed Jun. 9, 2008.

* cited by examiner

*Primary Examiner* — Teresa E Strzelecka
(74) *Attorney, Agent, or Firm* — Logue PC

(57) ABSTRACT

This invention provides compositions and methods for rapid isolation and purification of nucleopolymers from biological samples using anionic exchange media. The method of this invention can utilize commercially available anion exchanger materials with selected solutions of known ionic strength for absorption and elution. The medium/nucleoprotein bound complex may be optionally stored or transported, and is subsequently treated with eluents to remove undesirable proteins and inorganic salts. The partially purified complex may also be stored or transported. This method is particularly advantageous since it allows rapid isolation and purification of soluble nucleic acids from a large volume of biological fluids with easy handling and storage, stabilizing the samples against degradation prior to analysis. It also permits the purification and identification of shorter fragments of nucleic acids from bodily fluids which, until now, had not been identified. The method is widely useful to prepare samples formats that are convenient in diagnostic analytical methods.

11 Claims, 13 Drawing Sheets

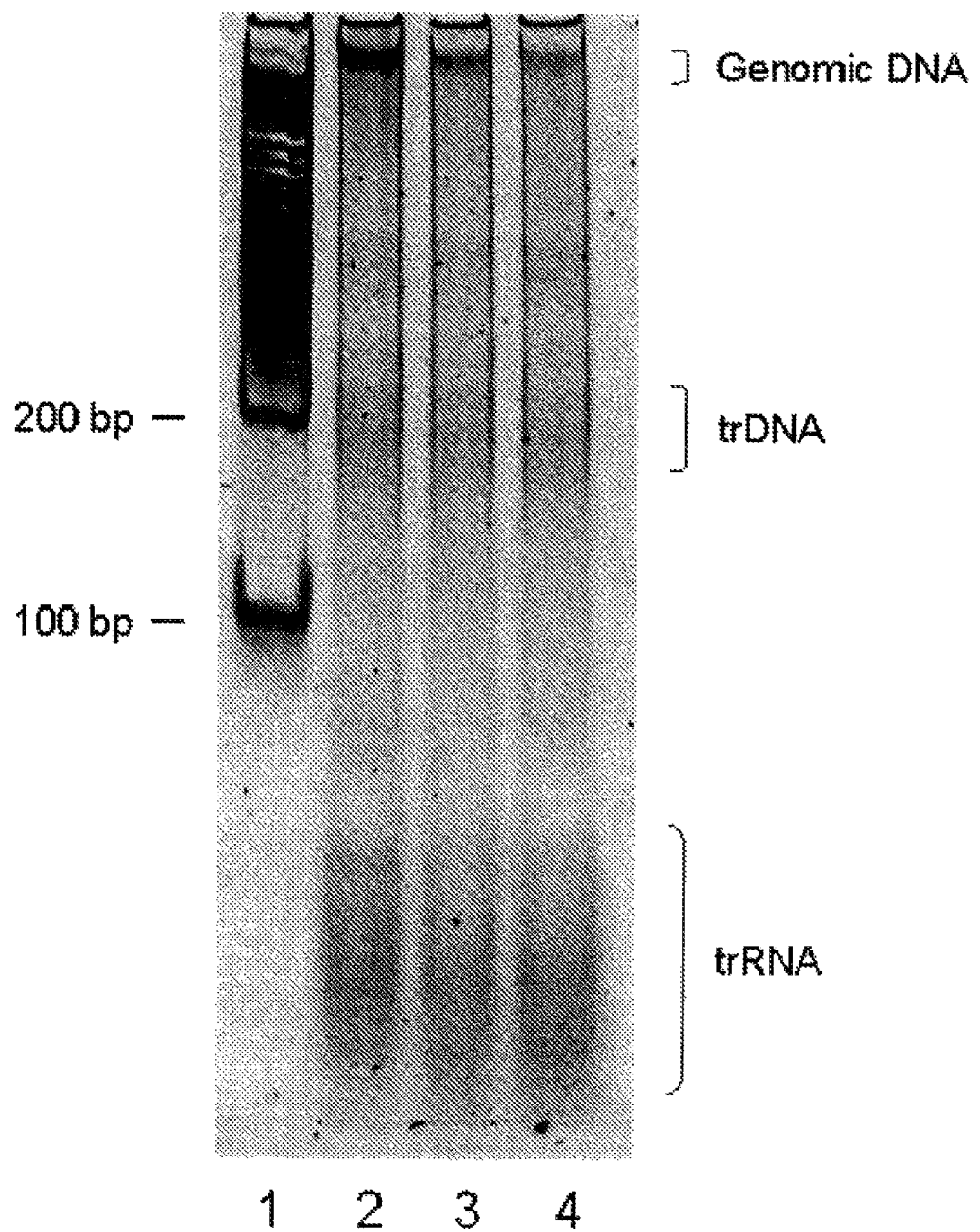

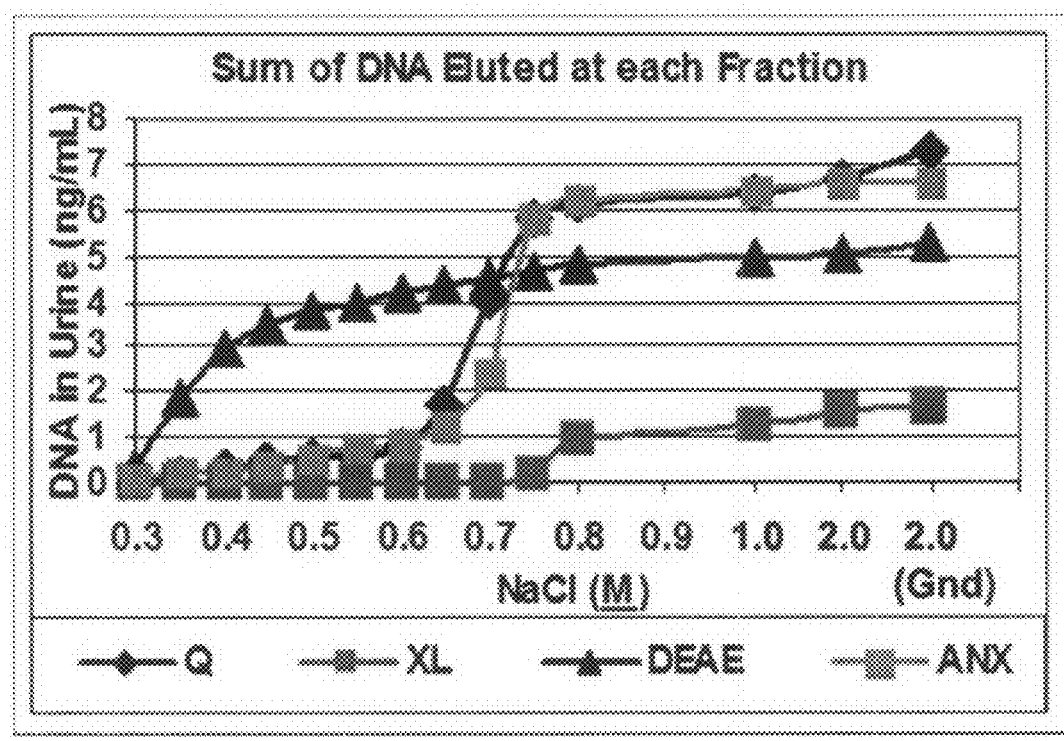

Lane Sample
1) Marker
2) Blank
3) T=0
4) Marker
5) 4 days dry
6) 7 days dry
7) 11 days dry
8) 4 days wet
9) 7 days wet
10) 11 days wet Dry – no buffer with resin
Wet – resin stored in buffer Stability of DNA Adsorbed on Resin

SEQUENCE LISTING

```
<160> NUMBER OF SEQ ID NOS: 6
<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 1
ccctggagaa gagctacgag                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<400> SEQUENCE: 2
aggaaggctg gaagagtgc                                               19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgacggccag gtcatcacca                                              20

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actttatgaa aacccacgtt gagc                                         24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccagaagcca cgcccattag                                              20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tgggtaatgc gcgggttgtc cttt                                         24
```

COMPOSITIONS, METHODS AND KITS FOR ISOLATING NUCLEIC ACIDS FROM BODY FLUIDS USING ANION EXCHANGE MEDIA

CROSS-REFERENCE TO RELATED APPLICATIONS

This application claims priority from U.S. Provisional Application Ser. No. 60/850,839 filed on Oct. 10, 2006, which is incorporated herein by reference in its entirety.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates generally to the rapid separation, isolation, and purification of cell-free nucleic acids, DNA and/or RNA, from biological samples. The method can be particularly concerned with the rapid and simple purification of nucleic acids from bodily fluids or tissues for clinical diagnosis, and disease and treatment monitoring.

BACKGROUND OF THE INVENTION

Modern molecular biology requires the isolation of nucleic acids from a variety of sources comprising complex nucleic acids mixture with other compounds such as proteins, lipids and other cellular constituents. Particularly important examples of such mixtures include soluble nucleoproteins, which consist of nucleic acid molecules of varying length, complexed with proteins, e.g., histones. These complexes can be released into the bloodstream as a result of the normal apoptosis or other forms of cell death. It has been shown that eventually they cross the kidney barrier (Tr-DNA/RNA) and can be detected in the urine (Umansky, S. R., et al. 1982, Biochim. Biophys. Acta 655:9-17; Lichstenstein, A. V., et al. 2001, Ann NY Acad Sci, 945:239-249; Umansky, S & Tomei, D. 2006 Expert Rev. Mol. Diagn. 6:153-163). Because they are soluble, and released from cells throughout the body they can be useful as indicators for the detection and monitoring of diseases and abnormal conditions which may be present in areas of the body other than where the fluid is obtained (Al-Yatama et al. 2001, Prenat Diagn, 21:399-402, Utting, M., et al. (2002), Clin Cancer Res, 8:35-40). Most of currently existing technologies can be designed for isolation of high molecular weight cellular DNA and RNA. These methods require several steps. First, cells must be lysed. Second, nuclease activity has to be inhibited to prevent degradation of the released nucleic acids. Third, the nucleic acids should be separated from proteins. This deproteinization step may include extraction with a variety of organic solvents, including phenol and/or chloroform, followed by precipitation with ethanol, (Maniatis et al., "Molecular Cloning. A Laboratory Manual". Cold Spring Harbor Laboratory, Cold Spring Harbor, N.Y.). Another method for nucleic acids extraction can be based on their adsorption on silica from highly concentrated solutions of chaotropic agents with subsequent elution at a low ionic strength. These conventional methods suffer from the disadvantages of being time-consuming and laborious, and they can also involve the use of chemical reagents that are hazardous and/or toxic to the worker and/or the environment.

Purification of DNA and/or RNA from cell free nucleoprotein complexes may not require the cell lysis step. However, there is a large body of evidence showing that the cell free circulating nucleic acids in bodily fluids can be present in very low concentrations and are fragmented to the average size of 150-300 bp, which introduces additional requirements to a purification procedure. First, for a large specimen volume it can be technically difficult to perform phenol deproteinization, automation of the process is almost impossible, and use of extremely toxic phenol in clinical lab setting is impractical. Silica-based methods may be much more suitable for isolation of nucleic acids from diluted solutions. However, first, significant additional dilution of original nucleic acid solution can be necessary to get high enough concentration of a chaotropic agent, and DNA isolation from large volumes becomes a problem. Second, binding of single stranded and short nucleic acid fragments (less than 200 bp) to silica is not very effective, and they can be lost during purification.

Anion exchange media has also been used for the fractionation and isolation of nucleic acids, although the biological sample containing them is usually first been processed to free the nucleic acids from other cellular components (Yamakawa et al., Analytical Biochemistry, 24:242-250 (1996).

There remains an unmet need in the art for a novel method of isolating and preserving cell-free nucleic acids from body fluids wherein such method avoids multiple proceeding to free the nucleic acids from cellular material, provides nucleic acid sequences of various lengths, preserves the integrity of nucleic acids and is readily adaptable to high-throughput of samples for the diagnostic analysis.

SUMMARY OF THE INVENTION

The present invention relates in part to novel method of rapid separation, isolation, and purification of cell-free DNA or RNA from biological samples. Indeed, cell-free high and low molecular weight nucleic acids have been successfully separated, isolated and purified with the methods of the present invention. The instant method can be particularly advantageous for resolving cell-free low molecular weight DNA or RNA (<40 base pairs and as low as 10 base pairs) found in samples of human bodily fluids, such as for example urine, blood plasma, cerebrospinal fluid, amniotic fluid and saliva.

In some embodiments, the invention relates to the method of substantially isolating nucleic acids from a sample of body fluid, for example urine or blood plasma, comprising:

a) selecting an anion exchange material which effectively adsorbs said target nucleic acids or proteinous complexes thereof.

The methods of the present invention can utilize commercially available anion exchange materials. Either strong or weak anion exchangers may be employed. A preferred weak exchanger can be one in which primary, secondary, or tertiary amine groups (i.e., protonatable amines) provide the exchange sites. The strong base anion exchanger has quaternary ammonium groups (i.e., not protonatable and always positively charged) as the exchange sites. Both exchangers can be selected in relation to their respective absorption and elution ionic strengths and/or pH for the DNA or RNA being separated. Purification by anion exchange chromatography is described in EP 0 268 946 B1 which is incorporated by reference herein.

The material which is commercially available under the designation Q-Sepharose™ (GE Healthcare) is a particularly suitable for the methods of the present invention.

Q-Sepharose™, can be a strong anion exchanger based on a highly cross-linked, bead formed 6% agarose matrix, with a mean particle size of 90 μm. The Q-Sepharose™ can be stable in all commonly used aqueous buffers with the recommended pH of 2-12 and recommended working flow rate of 300-500 cm/h. In other preferred embodiments, the anion-exchange medium can be selected from sepharose-based quaternary ammonium anion exchange medium such as Q-filters or Q-resin.

The chromatographic support material for the anion charge used in the instant methods can be a modified porous inorganic material. As inorganic support materials, there may be used materials such as silica gel, diatomaceous earth, glass, aluminium oxides, titanium oxides, zirconium oxides, hydroxyapatite, and as organic support materials, such as dextrane, agarose, acrylic amide, polystyrene resins, or copolymers of the monomeric building blocks of the polymers mentioned.

The nucleic acids can also be purified by anion exchange materials based on polystyrene/DVB, such as Poros 20 for medium pressure chromatography, Poros™. 50 HQ, of the firm of BioPerseptive, Cambridge, U.S.A., or over DEAE Sepharose™, DEAE Sephadex™ of the firm of Pharmacia, Sweden; DEAE Spherodex®, DEAE Spherosil™, of the firm of Biosepra, France.

b) applying body fluid sample, such as urine or blood plasma, containing nucleic acids or their proteinous complexes to the selected anion exchange material, and said nucleic acids or their complexes becoming adsorbed to said column material.

The contact and subsequent adsorption onto the resin can take place by simple mixing of the anion exchange media with the body fluid, with the optional addition of a solvent, buffer or other diluent, in a suitable sample container such as a glass or plastic tube, or vessel commonly used for handling biological specimens. This simple mixing referred to as batch processing, can be allowed to take place for a period of time sufficiently long enough to allow for binding of the nucleoprotein to the media, preferably 10 to 40 min. The media/complex can then be separated from the remainder of the sample/liquid by decanting, centrifugation, filtration or other mechanical means.

c) optionally washing said anion exchange material with an aqueous solution of a salt at which the nucleic acids remain bound to said anion exchange material, said washing being of sufficient volume and ionic strength to wash the non-binding or weakly binding components through said anion-exchange material. In some embodiments, the resin can be washed with 2×SSC (300 mM NaCl/30 mM sodium citrate (pH 7.0). Preferred ranges of the salt solutions are 300-600 nM NaCl/30 mM sodium citrate (pH 7.0) In other preferred embodiments, the resin can be washed with 300 mM LiCl/10 mM NaOAc (pH 5.2). Preferred ranges of the salt solutions are 300-600 mM LiCl/10 mM NaOAc (pH 5.2).

d) eluting the bound nucleic acids by passing through said anion exchange material an aqueous solution of increasing ionic strength to remove in succession proteins that are not bound or are weakly bound to the anion-exchange material and said nucleic acids of increasing molecular weight from the column. In some preferred embodiments, both proteins and high and low molecular weight nucleic acids (as low as 10 base pairs) can be selectively eluted from the resin stepwise with the salt solution of concentrations from 300 mM to 2.0 M of NaCl and finally with 2.0 M guanidine isothiocyanate. In other preferred embodiments, LiCl solutions in the concentration range of 300 mM to 2.0 M of LiCl are used for stepwise elution.

e) analyzing the eluted nucleic acid fraction.

The nucleic acids eluted preferably by the methods of the instant invention are in the size range of 766-25 base pairs, more preferably in the size range of 10-100 base pairs, and most preferably in the size range of less then 40 base pairs. The smallest size range of the fragment eluted by the methods of the instant invention are 10 base pairs. The primers for amplifying nucleic acids are preferably obtained from the genes which are to be analyzed, i.e. from oncogenes, tumor suppressor genes and/or micro-satellite, for example, or they may be suitable for amplifying viral or bacterial nucleic acid sequences. Enzymes and restriction endonucleases suitable for amplifying nucleic acids are known and commercially available.

In some embodiments, the nucleic acids isolated by the methods of the present invention may be in double-stranded or single-stranded form.

In other embodiments, the body fluid containing the cell-free nucleic acid is amniotic fluid.

In yet other embodiments, the body fluid containing the cell-free nucleic acid is cerebrospinal fluid.

In some other embodiments, the body fluid containing the cell-free nucleic acid is blood plasma.

In yet other embodiments, the body fluid containing the cell-free nucleic acid is saliva.

In some embodiments, the body fluid, for example urine, can be pre-filtered through a membrane and supplemented with 10 mM EDTA (pH 8.0) and 10 mM Tris-HCL (pH 8.0) prior to adsorption onto the anion-exchange medium. Commercial sources for filtration devices include Pall-Filtron (Northborough, Mass.), Millipore (Bedford, Mass.), and Amicon (Danvers, Mass.). The following filtration devices may be used with the methods of the instant invention such as a flat plate device, spiral wound cartridge, hollow fiber, tubular or single sheet device, open-channel device, etc.

The surface area of the filtration membrane used can depend on the amount of nucleic acid to be purified. The membrane may be of a low-binding material to minimize adsorptive losses and is preferably durable, cleanable, and chemically compatible with the buffers to be used. A number of suitable membranes are commercially available, including, e.g., cellulose acetate, polysulfone, polyethersulfone, and polyvinylidene difluoride. Preferably, the membrane material is polysulfone or polyethersulfone.

In other embodiments, the body fluid, for example blood plasma, can be supplemented with EDTA and Tris-HCL buffer (pH 8.0) and digested with proteinases, such as for example Proteinase K, prior to adsorption onto the anion exchange medium.

In yet further embodiments, the anion-exchange medium can be immobilized on an individualized carrier wherein such a carrier is a column, cartridge or portable filtering system which can be used for transport or storage of the medium/nucleoprotein bound complex. In some embodiments, the nucleic acid/anion exchange is maintained in storage for up to 3 weeks.

The present invention also comprises a kit with solid carrier capable of adsorbing the nucleic acids containing in a sample of a body fluid, for example urine and blood plasma.

The kit is also claimed containing components necessary for performing the process according to the invention. These include, in particular, reagents, also in concentrated form for final mixing by the user, chromatographic materials for the separation of the nucleic acids, aqueous solutions (buffers, optionally also in concentrated form for final adjusting by the user) or chromatographic materials for desalting nucleic acids which have been eluted with sodium chloride.

Preferably, the reagent kit contains additional means for purifying nucleic acids which comprise, for example, inorganic and/or organic carriers and optionally solutions, excipients and/or accessories. Such agents are known from the prior art (for example WO 95/01359) and are commercially available. Inorganic components of carriers may be, for example, porous or non-porous metal oxides or mixed metal oxides, e.g. aluminium oxide, titanium dioxide, iron oxide or zirconium dioxide, silica gels, materials based on glass, e.g. modified or unmodified glass particles or ground glass, quartz, zeolite or mixtures of one or more of the above-mentioned substances. On the other hand, the carrier may also contain organic ingredients which may be selected, for example, from latex particles optionally modified with functional groups, synthetic polymers such as polyethylene, polypropylene, polyvinylidene fluoride, particularly ultra high molecular polyethylene or HD-polyethylene, or mixtures of one or more of the above-mentioned substances.

In addition, the reagent kit according to the invention may also contain excipients such as, for example, a protease such as proteinase K, or enzymes and other agents for manipulating nucleic acids, e.g. at least one amplification primer, and enzymes suitable for amplifying nucleic acids, e.g. a nucleic acid polymerase and/or at least one restriction endonuclease.

The primers for amplifying nucleic acids are preferably obtained from the genes which are to be analysed, i.e. from oncogenes, tumor suppressor genes and/or micro-satellite, for example, or they may be suitable for amplifying viral or bacterial nucleic acid sequences. Enzymes and restriction endonucleases suitable for amplifying nucleic acids are known and commercially available.

Other features and advantages of the invention will be apparent from the following detailed description and claims.

DESCRIPTION OF THE FIGURES

FIG. 3 is a photograph of a polyacrylamide gel showing purification of nucleic acids with Q-Sepharose using whole or filtered urine.

FIGS. 4A and 4B are photographs of graphical illustration of DNA elution profile from anion exchange resin. The following anion exchange media were tested: DEAE, Q, XL, and ANX.

DETAILED DESCRIPTION OF THE INVENTION

Figure 1:
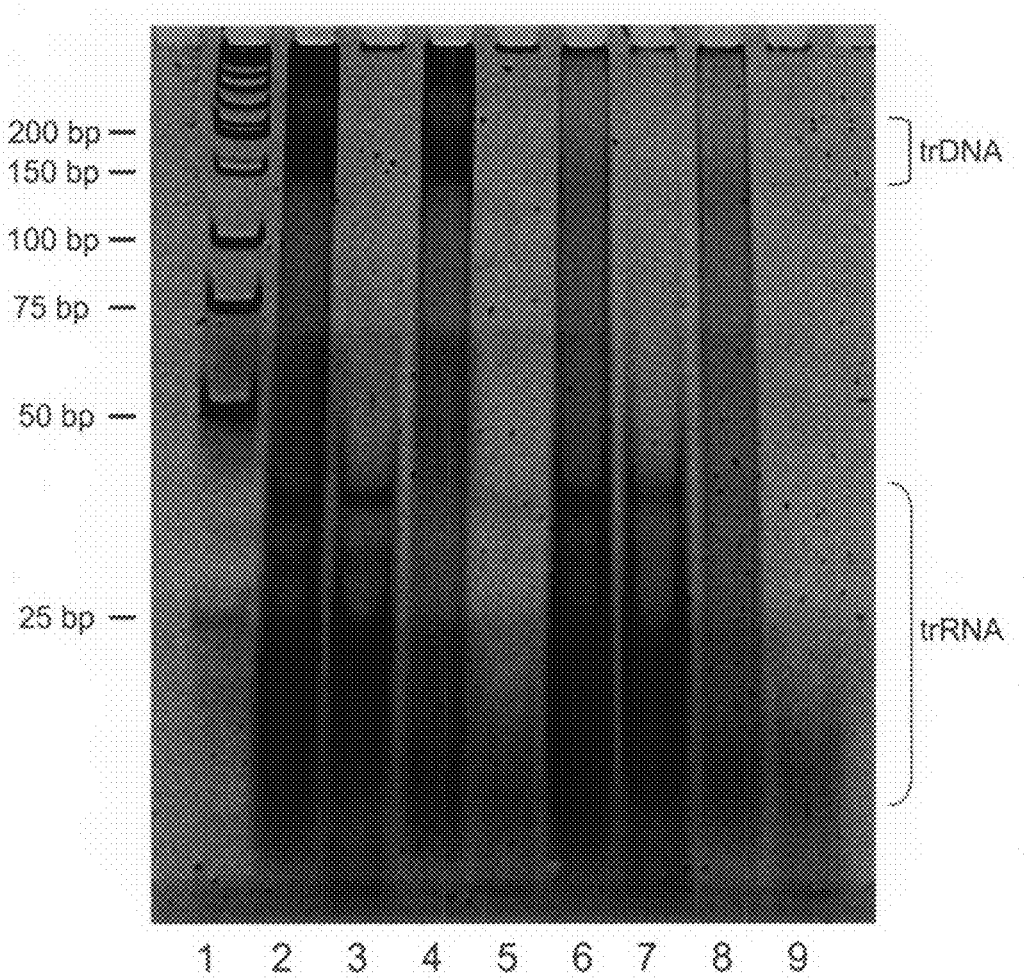
FIG. 1 is a photograph of a polyacrylamide gel demonstrating the separation and characterization of DNA and RNA isolated from urine by ion exchange chromatography on Q-Sepharose™.

The invention is based in part upon the discovery that cell-free nucleic acids may be detected in body fluids of a subject. This invention provides methods for the isolation, stabilization and purification of the cell-free nucleic acids. There are several important advantages of the proposed method. First, simultaneous concentration and partial purification of cell-free nucleic acids can be achieved. This is particularly advantageous when the volume of body fluid sample is large but the concentration of nucleic acid in the sample is low. Second, absorption behavior is not dependent on the molecular weight of nucleic acids, allowing the isolation of short fragments of lower molecular weight (<40 base pairs and as low as 10 base pairs) present in cell-free nucleoproteins. Further, the anion exchange media i.e. resins or filters, containing adsorbed cell-free nucleic acid material can be used to transport and store samples. Adsorption to anion exchange media substantially separate nucleic acids from nucleases usually present in bodily fluids. Once adsorbed, nucleic acids can be stable for at least 10 days at room temperature.

The methods of the instant invention are suitable for detecting cell-free nucleic acid of interest, including low-molecular weight fragments, in a body fluid, such as blood, amniotic fluid, cerebrospinal fluid, plasma, mother's milk, semen, lymph fluid, serum, sputum, liquor, saliva and urine.

In some embodiments, the invention relates to the method of substantially isolating nucleic acids from a sample of body fluid, for example urine or blood plasma, comprising the step of selecting an anion exchange material which effectively adsorbs said target nucleic acids or proteinous complexes thereof.

The methods of the present invention can utilize commercially available anion exchange materials. Either strong or weak anion exchangers may be employed. A preferred weak exchanger can be one in which primary, secondary, or tertiary amine groups (i.e., protonatable amines) provide the exchange sites. The strong base anion exchanger has quaternary ammonium groups (i.e., not protonatable and always positively charged) as the exchange sites. Both exchangers can be selected in relation to their respective absorption and elution ionic strengths and/or pH for the DNA or RNA being separated.

The material which is commercially available under the designation Q-Sepharose™ (GE Healthcare) is a particularly suitable for the methods of the present invention.

Q-Sepharose™, can be a strong anion exchanger based on a highly cross-linked, bead formed 6% agarose matrix, with a mean particle size of 90 μm. The Q-Sepharose™ can be stable in all commonly used aqueous buffers with the recommended pH of 2-12 and recommended working flow rate of 300-500 cm/h. In other preferred embodiment, the anion-exchange medium can be selected from sepharose-based quaternary ammonium anion exchange medium such as Q-filters or Q-resin.

The nucleic acids can also be purified by anion exchange materials based on polystyrene/DVB, such as Poros 20 for medium pressure chromatography, Poros™ 50 HQ, of the firm of BioPerseptive, Cambridge, U.S.A., or over DEAE Sepharose™, DEAE Sephadex™ of the firm of Pharmacia, Sweden; DEAE Spherodex™, DEAE Spherosil™, of the firm of Biosepra, France. Other examples of sepharose-based resins, functionalized with cationic ammonium groups which can be used include Sepharose™ Fast Flow, DEAE-Sepharose™, Q Sepharose-XL™ DEAE Sepharose Fast Flow (GE Healthcare).

The instant method includes applying body fluid sample, such as urine or blood plasma, containing nucleic acids or their proteinous complexes to the selected anion exchange material, and said nucleic acids or their complexes becoming adsorbed to said column material.

The contact and subsequent adsorption onto the resin can take place by simple mixing of the anion exchange media with the body fluid, with the optional addition of a solvent, buffer or other diluent, in a suitable sample container such as a glass or plastic tube, or vessel commonly used for handling biological specimens. This simple mixing referred to as batch processing, can be allowed to take place for a period of time sufficiently long enough to allow for binding of the nucleoprotein to the media, preferably 10 to 40 min. The media/complex can then be separated from the remainder of the sample/liquid by decanting, centrifugation, filtration or other mechanical means.

The methods of the instant invention also involves optionally washing said anion exchange material with an aqueous solution of a salt at which the nucleic acids remain bound to said anion exchange material, said washing being of sufficient volume and ionic strength to wash the non-binding or weakly binding components through said anion-exchange material. In some embodiments, the resin can be washed with 2×SSC (300 mM NaCl/30 mM sodium citrate (pH 7.0). Preferred ranges of the salt solutions are 300-600 nM NaCl/30 mM sodium citrate (pH 7.0). In other preferred embodiments, the resin can be washed with 300 mM LiCl/10 mM NaOAc (pH 5.2). Preferred ranges of the salt solutions are 300-600 mM LiCl/10 mM NaOAc (pH 5.2).

The elution of the bound nucleic acids involves passing through said anion exchange material an aqueous solution of increasing ionic strength to remove in succession proteins that are not bound or are weakly bound to the anion-exchange material and said nucleic acids of increasing molecular weight from the column. By employing a solution at known ionic strength for the initial binding of the nucleic acids to the anion exchange resin, most of the water soluble components including other electronegative molecules such as proteins (weakly-bound contaminants) can be washed through the column. For elution, the required ionic strength can be reached by using known concentrations of a salt such as NaCl, which may be mixed with a buffer to control pH, ideally corresponding to the lowest ionic strength at which the nucleic acids may completely elute. Contaminating substances bound to the anion exchange resin with higher stringency than the nucleic acids may thereby be left attached to the resin, i.e., stronger bound contaminants can be separated away from the nucleic acids.

In some preferred embodiments, both proteins and high and low molecular weight nucleic acids (as low as 10 base pairs) can be selectively eluted from the resin stepwise with the salt solution of concentrations from 300 mM to 2.0 M of NaCl and finally with 2.0 M guanidine isothiocyanate. In other preferred embodiments, LiCl solutions of concentrations from 300 mM to 2.0 M are used for stepwise elution.

The methods of the instant invention also involve analyzing the eluted nucleic acid fraction. The nucleic acid eluted are preferably in the size range of 766-25 base pairs, more preferably in the size range of 10-100 base pairs, and most preferably in the size range of less then 40 base pairs. The smallest size range of the fragment eluted by the methods of the instant invention are 10 base pairs. The primers for amplifying nucleic acids are preferably obtained from the genes which are to be analyzed, i.e. from oncogenes, tumor suppressor genes and/or micro-satellite, for example, or they may be suitable for amplifying viral or bacterial nucleic acid sequences. Enzymes and restriction endonucleases suitable for amplifying nucleic acids are known and commercially available.

In some embodiments, the nucleic acids isolated by the methods of the present invention may be in double-stranded or single-stranded form.

In other embodiments, the body fluid containing the cell-free nucleic acid is amniotic fluid.

In yet other embodiments, the body fluid containing the cell-free nucleic acid is cerebrospinal fluid.

In some other embodiments, the body fluid containing the cell-free nucleic acid is blood plasma.

In yet other embodiments, the body fluid containing the cell-free nucleic acid is saliva.

In some embodiments, the body fluid, for example urine, can be pre-filtered through a membrane and supplemented with 10 mM EDTA (pH 8.0) and 10 mM Tris-HCL (pH 8.0) prior to adsorption onto the anion-exchange medium. The filtering step removes any insoluble debris that may be present. Such debris or insoluble material, for example, may result if the biological sample has been stored (archived) in a frozen state for a prolonged period. Commercial sources for filtration devices include Pall-Filtron (Northborough, Mass.), Millipore (Bedford, Mass.), and Amicon (Danvers, Mass.). The following filtration devices may be used with the methods of the instant invention such as a flat plate device, spiral wound cartridge, hollow fiber, tubular or single sheet device, open-channel device, etc.

The surface area of the filtration membrane used can depend on the amount of nucleic acid to be purified. The membrane may be of a low-binding material to minimize adsorptive losses and is preferably durable, cleanable, and chemically compatible with the buffers to be used. A number of suitable membranes are commercially available, including, e.g., cellulose acetate, polysulfone, polyethersulfone, and polyvinylidene difluoride. Preferably, the membrane material is polysulfone or polyethersulfone.

In other embodiments, the body fluid, for example blood plasma, can be supplemented with EDTA and Tris-HCL buffer (pH 8.0) and digested with proteinase, for example with Proteinase K, prior to adsorption onto the anion exchange medium.

In yet further embodiments, the anion-exchange medium can be immobilized on an individualized carrier wherein such a carrier is a column, cartridge or portable filtering system which can be used for transport or storage of the medium/nucleoprotein bound complex. In some embodiments, the nucleic acid/anion exchange is maintained in storage for up to 3 weeks.

The nucleoprotein/anion exchange complex, whether prepared in a batch mode or in an immobilized form, may be treated with an eluent to wash off any remaining unbound material, such as proteins with less negative net charge and inorganic salts. It may also be used as a means to store the nucleoprotein/nucleic acids. The complex may also be optionally treated with a solvent miscible with water in order to dry the resin, which can then be stored for extended periods prior to ultimate desorption and analysis.

The nucleic acid/anion exchange complex may also serve as the storage container for the sample. For example, the body fluid, obtained from a patient may be send to the laboratory for testing, usually kept frozen to prevent degradation, but the sample may also be applied to the immobilized anion exchange medium at or nearby the site of sample collection. The nucleoprotein/anion exchange complex, e.g., the cartridge, tube or column containing the nucleoprotein sample can be prepared at the site of collection and sent directly to the laboratory for analysis.

For detection of a nucleic acid of interest, DNA or RNA an amplification step (such as PCR or RT-PCR) may be used. In one embodiment, the reaction comprises real-time monitored amplification. In another embodiment the nucleic acid detection and/or quantification is performed with an end-point read-out system. Such systems may comprise a calorimetric detection, an enzymatic assay, and/or a dipstick.

The invention also comprises a kit of parts for detecting, identifying and/or quantifying a nucleic acid of interest in a sample, comprising: a solid carrier capable of at least in part absorbing the cell free nucleoprotein complexes from a sample; and a set of solutions for subsequent resin wash and nucleic acid elution. In some embodiment, the kit could contain the carrier itself that can absorb the bodily fluid, linked to a part of paper or surface on which information can be written or printed, e.g., information about the patient, date of sampling or more dates of sampling, therapy regimen, barcodes, ID-numbers, etc. Such a surface for this type of information is unequivocally linked at the carrier with a sample, thereby making sample tracking more convenient and reliable. Typically, this type of surface can contain much more information than a tube can hold. In another embodiment, the carrier can be a Q-resin containing cartridge with a standard luer connector. A sample of body fluid can be passed through the cartridge and after washing with NaCl, the cartridge can be sent to a clinical lab where nucleic acids will be eluted and analyzed.

In some embodiment, the kit further comprises means for nucleic acid amplification. The means may comprise of components for real-time monitored amplification, and/or components for amplification with end-point detection/quantification. A kit of parts of the invention can be useful in resource-poor countries with a few hospitals. Such hospitals can distribute the solid carriers, such as filter papers, among inhabitants in remote areas. Once samples are collected, they can be stored at ambient temperature and transported hospitals. If the hospital can be properly equipped, the samples can be investigated using the kit supplemented with the nucleic acid isolation solutions and components for analysis. Of course, also hospitals in developed countries can use a kit of part of the invention for collecting and testing a sample.

A kit of parts for detection, identification and/or quantification may contain a collection of materials necessary to safely draw the bodily fluid from the patient. With external bodily fluids e.g. urine, mother's milk or saliva, appropriate safety precautions should be taken than when internal bodily fluids are samples like blood, plasma, serum, or lymph drain. For the internal bodily fluids, one can compose a kit that contains a solid carrier capable of at least in part absorbing the sample, and a nucleic acid isolation solution, next to a pair of examination gloves, a alcohol swab to clean the skin, a finger or heel puncture device, a bandage, an envelope, e.g., with the address of the destination laboratory as well as with a space for an identification number or patient code, and coated inside for safe postal transportation, and a desiccator to keep the sample dry and to prevent it from fungal or bacterial growth. Other possibilities for the collection device could comprise specially designed devices for one-time use, like a device described in patent number U.S. Pat. No. 5,139,742: Disposable liquid testing device by Livestock Control Holding B.V. in Amersfoort, the Netherlands. Any combination of these items, or replaced for other type of items/devices to be used for storage and/or transportation of any nucleic acid containing bodily fluids is possible.

In the preferred embodiment, the kit can be based on direct adsorption of urinary nucleic acid/nucleoproteins on an anion-exchanger, preferably Q-Sepharose®, followed by elution, which can include DNA/RNA fractionation step(s).

To facilitate understanding of the invention a number of terms are defined below:

The term "target" nucleic acid is a nucleic acid sequence to be evaluated by hybridization, amplification or any other means of analyzing a nucleic acid sequence, including a combination of analysis methods.

The term "probe" as used herein refers to an oligonucleotide (i.e., a sequence of nucleotides), whether occurring naturally produced synthetically, which forms a duplex structure or other complex with a sequence in another nucleic acid, due to complementarity or other means of reproducible attractive interaction, of at least one sequence in the probe with a sequence in the other nucleic acid. Probes are useful in the detection, identification and isolation of particular gene sequences. It is contemplated that any probe used in the present invention will be labeled with any "reporter molecule," so that it is detectable in any detection system, including, but not limited to, enzyme (e.g., ELISA, as well as enzyme-based histochemical assays), fluorescent, radioactive, and luminescent systems. It is further contemplated that the oligonucleotide of interest (i.e., to be detected) will be labeled with a reporter molecule. It is also contemplated that both the probe and oligonucleotide of interest will be labeled. It is not intended that the present invention be limited to any particular detection system or label.

The term "label" as used herein refers to any atom or molecule which can be used to provide a detectable (preferably quantifiable) signal, and which can be attached to a nucleic acid or protein. Labels provide signals detectable by any number of methods, including, but not limited to, fluorescence, radioactivity, colorimetry, gravimetry, X-ray diffraction or absorption, magnetism, and enzymatic activity.

The term "substantially single-stranded" when used in reference to a nucleic acid target means that the target molecule exists primarily as a single strand of nucleic acid in contrast to a double-stranded target which exists as two strands of nucleic acid which are held together by inter-strand base pairing interactions.

As used herein, the terms "substantially purified" and "substantially isolated" refer to nucleic acid sequences that are removed from their natural environment, isolated or separated, and are preferably 60% free, more preferably, 75% free, and most preferably 90% free from other components with which they are naturally associated. An "isolated polynucleotide" is therefore a substantially purified polynucleotide. It is contemplated that to practice the methods of the present invention polynucleotides can be, but need not be substantially purified. A variety of methods for the detection of nucleic acid sequences in unpurified form are known in the art.

"Amplification" is defined as the production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). As used herein, the term "polymerase chain reaction" ("PCR") refers to the method of K. B. Mullis (U.S. Pat. Nos. 4,683,195 and 4,683,202, hereby incorporated by reference), which describe a method for increasing the concentration of a segment of a target nucleic acid sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

Abbreviations and Acronyms:
ANX-4[also ANX Sepharose™ 4 Fast Flow (high sub)] Trademark of GE Healthcare Systems AB. A resin based on 4% highly cross-linked beaded agarose.
bp nucleotide base pair
DEAE diethylaminoethyl functional group
dATP 2'-deoxyadenosine 5'-triphosphate)
dCTP 2'-deoxycytidine 5'-triphosphate
dGTP 2-deoxyguanidine 5'-triphosphate
dNTP an equal molar mix of dATP, dCTP, dGTP, dTTP
dUTP 2'-deoxyuridine 5'-triphosphate
EDTA ethylenediaminetetraacetic acid
EtOH ethanol
GITC guanidine isothiocyanate
HPLC high performance liquid chromatography
PCR polymerase chain reaction
Q-membrane Anion exchange support with pendant quaternary amine functional groups in a cross-linked polymeric coating on a semi-permeable membrane. Manufacturers include Mustang and Sartorius.
Q-resin any of a number of ion exchange solid supports, including, but not limited to polymer (e.g. polystyrene) beads, ceramic particles, sepharose resins, and dextran resins, which are functionalized with quaternary ammonium groups.
Q-Sepharose™ A strong anion exchanger containing quaternary ammonium groups on a Sepharose support. Trademark of GE Healthcare Systems AB.
Q-Sepharose™ XL Q-sepharose resin modified to permit higher loading capacity. Trademark of GE Healthcare Systems AB DEAE Sephadex™ A-25 A weak anion exchanger containing the DEAE group on a dextran support. Trademark of GE Healthcare Systems AB.
Sepharose® A bead-formed agarose-based gel filtration matrix. Registered trademark of GE Healthcare Bio-Sciences AB.
SSC 150 mM NaCl/15 mM sodium citrate buffer, sometimes denoted 1×SSC; thus 2×SSC would be 300 mM NaCl/30 mM sodium citrate.
SYBR® Gold sensitive fluorescent stain available for detecting nucleic acids with standard ultraviolet transilluminators; SYBR is a registered trademark of MolecularProbes, Inc.
Taq (or Taq polymerase), a thermostable polymerase used in polymerase chain reaction to check for the presence or absence of a gene by amplifying a DNA fragment.
TE a mixture of (10 mM Tris-HCl (pH 8.0)/1 mM EDTA (pH 8.0).
Tr-DNA transrenal DNA, i.e., DNA that originates from outside the urinary tract and has crossed the renal barrier.
Tris (Tris Buffer) Tris hydroxymethylaminomethane.
TRIzol® A mono-phasic solution of phenol and guanidine isothiocyanate, used for isolation of RNA; a registered trademark of Molecular Research Center, Inc.
Tr-RNA transrenal RNA i.e., RNA that originates from outside the urinary tract and has crossed the renal barrier.
U Units of activity of an enzyme, such as Taq.
Wizards® Silica gel-based DNA purification system, registered trademark of Promega Corporation.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from the following detailed description and claims.

EXAMPLES

All of the methodology described herein may be modified by the technician skilled in the field with no change in the basic principal idea.

Example 1

A) Isolation of DNA and RNA from Urine by Ion Exchange Chromatography on Q-Sepharose™

Urine preparation and Q Binding: For these experiments, urine (15 mL) from healthy volunteer was filtered through a 5.0 μm Millex-SV syringe filter (Millipore) and then supplemented with 10 mM EDTA (pH 8.0) and 10 mM Tris-HCl (pH 8.0). The urine was allowed to bind in batch mode for 10 min to 400 μl of unwashed Q-Sepharose™ (GE Healthcare) in a 50 mL centrifuge tube at room temperature. The resin was collected by centrifugation at ~1900 g for 5 min at room temperature in a table top clinical centrifuge using a swing bucket rotor. All but ~500 mL of supernatant was removed by aspiration. The resin pellet was resuspended in the remaining supernatant and transferred to a Micro Bio-Spin Chromatography Column (Bio-Rad). The resin (~150 μl packed volume) was collected by pulse centrifugation in a microfuge for ~10 sec (~10 k RPM) and the flow-through liquid discarded. The resin was washed three times with 500 µl 2×SSC (300 mM NaCL/30 mM sodium citrate (pH 7.0)).

Elution of Q-Sepharose™ bound nucleic acids: The bound nucleic acids were further eluted with three times resin bed volume of either of high salt solution [e.g. 1500 mM NaCl/150 mM sodium citrate (1×SSC) or 2 M LiCl] or TRIzol™ reagent (Invitrogen). When eluting with TRIzol™ it was necessary to cap the bottom of the column to prevent gravity flow.

TRIzol™ Phase Separation: The two 200 µl TRIzol eluates were pooled and 80 µl of $CHCl_3$/isoamyl alcohol (24:1) was added. The sample was shaken by hand and following a 3 min room temperature incubation, the sample was centrifuged at 12 k g for 15 min at 4° C. Exactly 240 µl of the upper aqueous phase was transferred to a fresh tube.

Precipitation of TRIzol™ eluted nucleic acids: The nucleic acids from the upper aqueous phase were precipitated at −20° C. for 30 min by the addition of 1 µl of 20 mg/mL glycogen (Roche) and 240 µl of 100% isopropyl alcohol. The precipitate was collected by centrifugation and the pellet washed twice with 200 µl of 70% ethanol. The pellet was allowed to air dry for 5 min at room temperature and then resuspended in 30 µl of 0.1 mM EDTA/1×RNA Secure (Ambion). The samples were incubated at 60° C. for 10 min to inactivate any residual RNase activity.

Silica based purification of TRIzol™ eluted nucleic acids (alternative to precipitation): To the upper aqueous phase add three volumes of 100% EtOH, mix well and incubate at room temperature for 5 min. Load the mixture onto an Axygen Bioscience silica minicolumn (Cat#2227), or equivalent, by centrifugation at 5,000 rmp for 1 minute (vacuum driven loading may be used instead).

Wash the silica column twice with 500 µL of 2 M LiCl/80% EtOH followed by additional two washes with 500 µL of 80 mM NaOAc pH 5.2/80% EtOH. Dry the spin column in a new Eppendorf tube by centrifugation at 10,000 rpm for 3 minutes. Elute the RNA with 50-60 µl of ddH2O.

Silica-based purification of high salt eluted nucleic acids: Three volumes of 100% EtOH were added to the high salt eluate, vortexed and incubated at room temperature for 5 min. The mixture was loaded by centrifugation onto an Axygen Bioscience silica minicolumn (Cat#:2227). Alternatively, vacuum manifold was used.

Silica column was washed twice with 500 µL of 2 M LiCl/10 mM NaAc (pH 5.2) in 70% EtOH followed with additional two washes with 500 µL of Wash buffer (75 mM KOAc pH 5.0, 80% EtOH). After the final wash the silica column was transfer into a new tube and centrifuge at 10,000 rpm for 3 minute. From silica column the nucleic acids was eluted with 50-60 µL of 1 mM Tris-HCl (pH 8.0)/0.025 mM EDTA (pH 8.0). To purify urine RNA from isolated total nucleic acids, the eluted fraction was digested with DNAse I as described in section below (see section DNAse I and RNAse A digestion).

DNase I and RNase A Digestion: For each sample, 50 µl of Q NaCl eluate was diluted with an equal volume of TE (10 mM Tris-HCl (pH 8.0)/1 mM EDTA (pH 8.0)) and precipitated at −20° C. for 30 min by the addition of 1 µl of 20 mg/mL glycogen (Roche) and 100 µl of 100% isopropyl alcohol. The precipitate was collected by centrifugation, washed twice with 200 µl of 70% ethanol and allowed to air dry for 5 min.

Specifically, for DNase I digestion the pellet was resuspended in 10 µl of 1×DNase I Reaction Buffer (NEB) containing 2 units of RNase free DNase I (NEB). Specifically, for RNase A digestion, the pellet was resuspended in 10 mL of deionized $H_2O$ containing 50 ng/mL boiled RNase A. For both digests samples were incubated at 37° C. for 60 min prior to the addition of loading dye and electrophoresis. All samples were subjected to electrophoresis on 5% polyacrylamide 1×TBE gels and stained with 1/10000 diluted SYBR® Gold (Invitrogen). The results of these experiments are summarized in FIG. 1 and clearly demonstrate that both DNA and RNA were isolated from urine ion exchange chromatography on Q-Sepharose™.

B) Isolation of Nucleic Acids from Urine Using Q-membrane™ Adsorbents.

Figure 2:
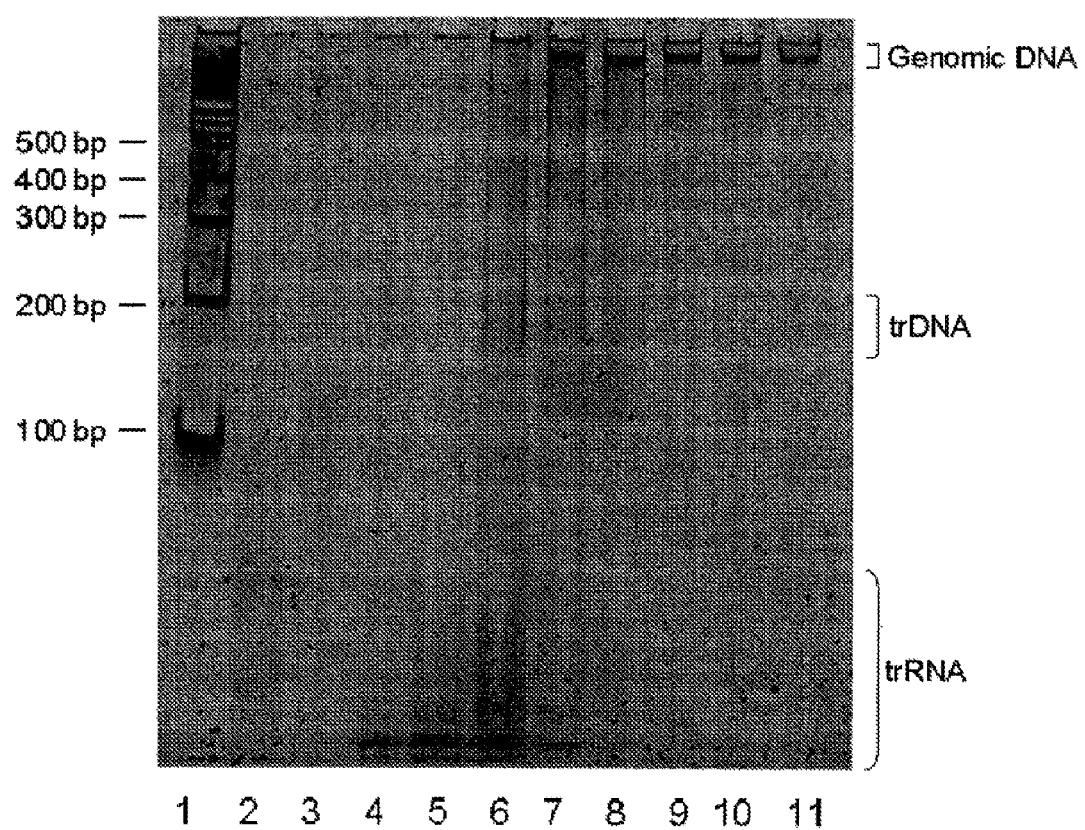
FIG. 2 is a photograph of a polyacrylamide gel showing nucleic acids isolated from urine using Q membrane adsorbents.

For these experiments, whole (unfiltered) urine from healthy volunteers (100 mL), supplemented with 5 mM EDTA (pH 8.0) and 10 mM Tris-HCl (pH 8.0) was applied to an MA5 Sartobind Q membrane adsorbent (Sartorious) pre-wet with 5 mL of Wash Buffer (5 mM EDTA (pH 8.0)/10 mM Tris-HCl (pH 8.0)) using a vacuum manifold. The membrane was washed with 5 mL of Wash Buffer and successively eluted with a 1 mL step gradient of 1×SSC to 10×SSC (1×SSC: 150 mM NaCl/15 mM NaCitrate (pH 7.0)). For each elution two 500 µl fractions were collected. The 100 µl of the second fraction from each step was diluted two fold with TE and precipitated by addition of an equal volume of 100% isopropanol using glycogen as carrier. All samples were subjected to electrophoresis on 5% polyacrylamide 1×TBE gels and stained with 1/10000 diluted SYBR® Gold (Invitrogen). As shown in FIG. 2 both DNA and RNA fragments, including small molecular weight fragments, were isolated using Q-membrane Adsorbents.

C) Purification of Urine Nucleic Acids Using Q-Sepharose™ for Either Whole or Filtered Urine.

Urine nucleic acid was isolated on Q-Sepharose™ by NaCl elution as described in the Example 1, Section A. However, for these experiments, urine sample was either not filtered (whole) or filtered through a 0.45 µm Millex-HV syringe filter (Millipore). Further, each sample was precipitated with isopropanol prior to electrophoresis as described in the Example 1, Section B, on 5% polyacrylamide 1×TBE gels and stained with 1/10000 diluted SYBR® Gold (Invitrogen). As shown in FIG. 3, the trDNA, trRNA and genomic DNA were detected in all samples analyzed regardless of whether or not the urine was filtered prior to adsorption onto the resin. It is also evident that there was a decrease in quantity of genomic DNA present in the filtered sample as compared to the unfiltered sample. There were no differences observed in the quantity of smaller RNA and smaller DNA isolated from filtered urine as compared to the unfiltered urine.

D) Comparison of Different Anion Exchange Resins

For these experiments, unfiltered urine (20 mL) was bound to approximately 400 µL of each resin by the batch method for 30 min (as summarized in Table 1). Resin volume was measured by addition of the commercially available resin slurry to a graduated cylinder or syringe, and decanting off the liquid. The mixtures were centrifuged for 5 min at 1900 g and the pelleted resin was then rinsed with 1 mL aliquots of increasing sodium chloride concentrations, with the final being 2 M NaCl (1.1) and then rinsed with 2 M guanidine thiocyanate. The collected fractions were precipitated with glycogen and isopropanol and re-suspended in 100 µL TE (10 mM Tris buffer and 1 mM EDTA).

TABLE 1

| Resin | GE Cat No. | Lot No. | Functional Group | Capacity | Capacity |
|---|---|---|---|---|---|
| DEAE-Sepharose™ | 17-0709-10 | 307354 | Diethylaminoethyl weak anion exchanger | 0.11-0.16 mmol (Cl$^-$)/mL | 110 mg HSA/mL medium |
| ANX-4 Sepharose™ | 17-1287-10 | 303229 | Diethylaminopropyl weak anion exchanger | 0.13-0.18 mmol (Cl$^-$)/mL | 5 mg thyroglobulin/mL medium |
| Q-Sepharose™ | 17-0510-10 | 310297 | Quaternary ammonium strong anion exchanger | 0.18-0.25 mmol (Cl$^-$)/mL | 120 mg HSA/mL medium |
| Q-Sepharose XL™ | 17-5437-10 | 303229 | Modified Quaternary ammonium strong anion exchanger | 0.18-0.26 mmol Cl$^-$/mL | >130 mg BSA/mL medium |

Further, the nucleic acid content of the purified fractions was determined by assaying for the nucleotide sequence coding for β-Actin, using real-time PCR. Most of the amplifiable template was eluted between 650 and 800 mM NaCl. Assay conditions for a 25 µL reaction were as follows: 3.0 mM MgCl$_2$, 0.2 mM d(A, G, C)TP, 0.4 mM dUTP, 0.2 µM primers, 0.1 µM probe, 10 mM Tris-HCl (pH 8.3), 5-mM KCl, 0.001% gelatin, and 0.3 U Taq (Jump Start, Sigma D4184). Following 1 minute at 95° C., the amplification was carried out 50 cycles of 30 seconds at 96° C. and 1 min at 60° C. The following primers (SEQ ID NOS 1-3, respectively, in order of appearance) were used in the PCR reactions:

```
Primers:
β-Actin forward      5'-CCCTGGAGAAGAGCTACGAG-3'

β-Actin reverse      5'-AGGAAGGCTGGAAGAGTGC-3'

β-Actin probe FAM    5'-TGACGGCCAGGTCATCACCA-3'
```

Figure 4A:
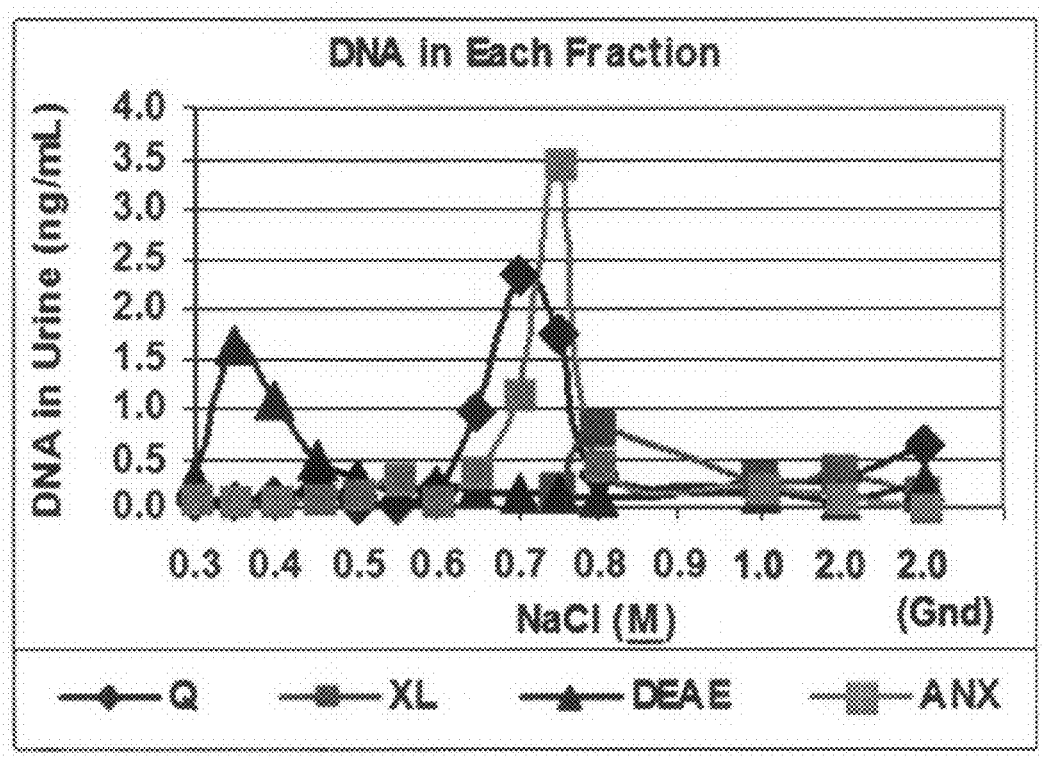

FIG. 4A shows the nucleic acid adsorption-elution behavior of each resin. For these experiments, nucleic acids were eluted from both Q-sepharose and ANX using 0.50-0.9 mM NaCl for elution. Elution of nucleic acids occurred for DEAE resin at 0.3 to 0.5 mM NaCl, and for XL resin at 0.75 mM to about 1.2 mM. FIG. 4B shows the total amount of nucleic acids which were recovered from each resin as the gradient of NaCl increased. As shown in FIGS. 4A and 4B, approximately the same amount of nucleic acid was recovered from ANX and Q-sepharose; lesser amounts of nucleic acid for DEAE, and significantly lesser amount for XL resin.

E) Step Gradient Elution of Nucleoprotein/Resin Complex

For these experiments, 20 mL sample of unfiltered urine was adsorbed to 400 µL of Q-Sepharose™ and eluted stepwise with 1 mL portions of NaCl solution with concentrations from 300 mM to 2.0 M, and finally with 2.0 M guanidine isothiocyanate. The fractions were collected, and subjected to PCR analysis and examined by 6% polyacrylamide gel electrophoresis. The gel was developed first using SYBR® Gold to visualize nucleic acids, and then with Silver stain to visualize proteins.

Figure 5:
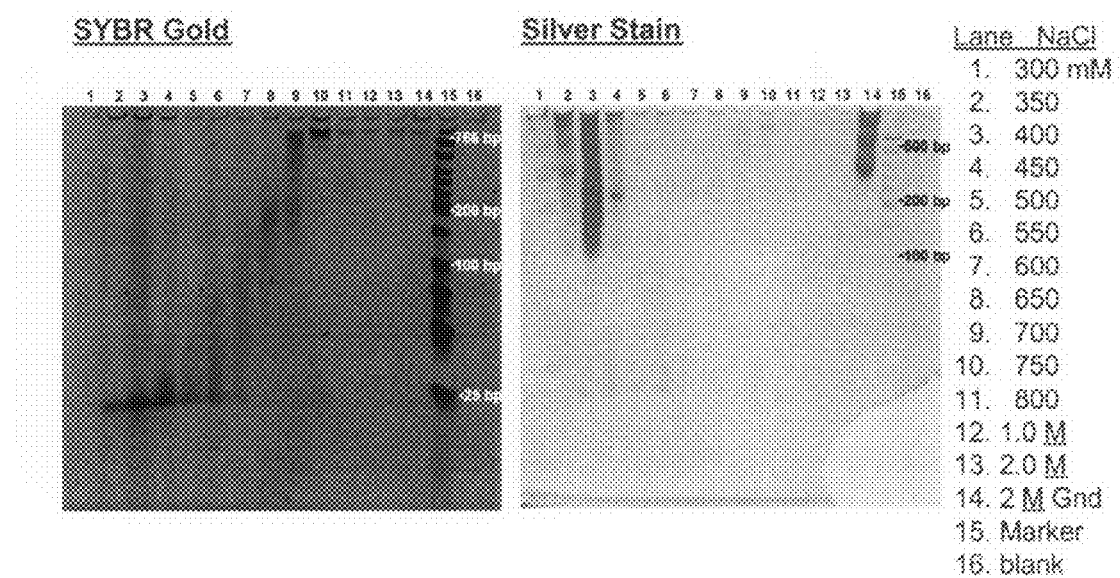
FIG. 5 is a photograph of a polyacrylamide gel showing elution profile of nucleic acid and protein from Q-Sepharose™.

As shown in FIG. 5, both proteins and nucleic acids can be selectively eluted from the resin and the content controlled by the NaCl concentration. For example, fractions 1-4 contained mainly proteins and low molecular weight nucleic acids, (<40 bp) fractions 5-8 contained mainly nucleic acids of (40-400 bp) and fractions 9 and above contained mainly higher molecular weight nucleic acids. Finally, the final fraction, obtained by elution with 2.0 guanidine isothiocyanate, contained proteins that were not eluted in earlier fractions.

F) Silica Column Fractionation of Urine Nucleic Acids

Nucleic acids eluted from Q-resin were separated to high and low molecular weight fractions as described below.

Figure 11:
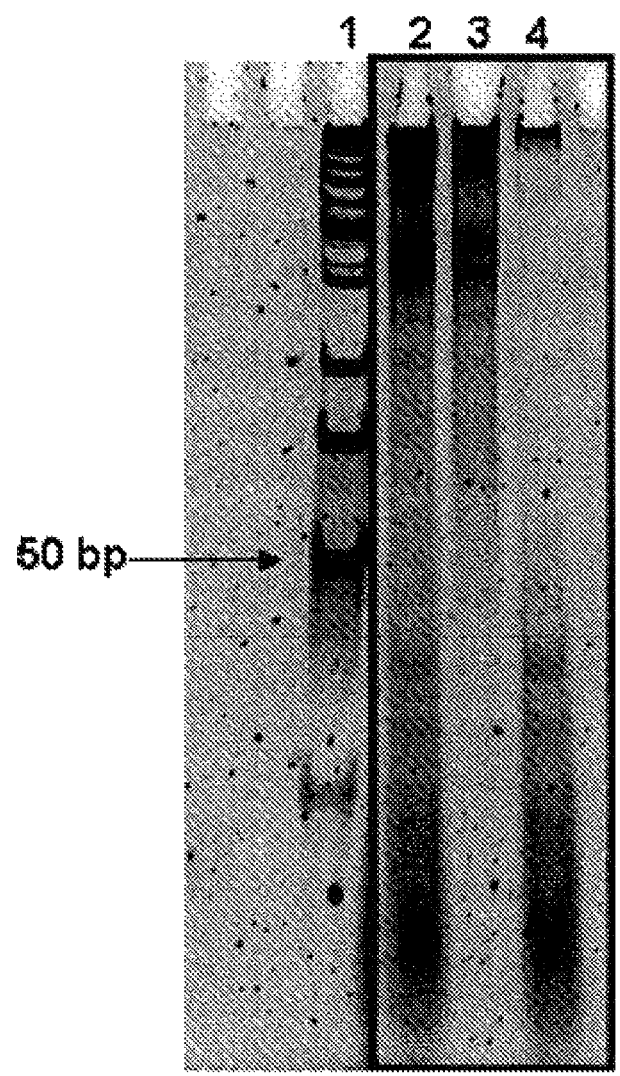
FIG. 11 is a photograph of polyacrylamide gel showing total, high molecular weight and low molecular weight nucleic acids fractionated on silica minicolumn.

High Molecular Weight Fraction (HMW):

To the high salt eluted nucleic acids equal volumes of 100% EtOH and 6M GuSCN (Guanidine isotiocyanate) solutions were added (up to final concentrations of 33% and 2 M, respectively). The mixture was incubate at room temperature for 5 min and applied to an Axigen silica minicolumn by centrifugation at 10,000 rpm for 1 min. Flow through fraction (FT) was collected for the following low molecular weight nucleic acids purification. Column was washed once with 500 µl of 2M LiCl/70% EtOH followed by two washes with 80 mM KOAc pH 5.0, 80% EtOH. The column was transferred to a new collection tube, centrifuged for 1 min at 10,000 rpm for 3 min to dry the membrane. Nucleic acids were eluted with 50 µl of 1 mM Tris-HCl (pH 8.0)/25 µM EDTA (pH 8.0) into a new collection tube as a HMW fraction. These results were summarized in FIG. 11.

Low Molecular Weight Fraction (LMU):

To the FT (see above) 100% EtOH was added to the final concentration of about 75%, mixed, incubated at room temperature for 5 min, and applied to an Axigen silica minicolumn by centrifugation at 10,000 rpm for 1 min. Further steps were identical to those described for HMW fraction. The results of these experiments are summarized in FIG. 11.

G) Stability of nucleic acids bound to the Q-Sepharose™

The effect of various conditions on the stability of nucleic acids bound to the Q-Sepharose™ column was studied, using β-Actin and Lambda as analytes. For these experiments, unfiltered urine (20 mL) and 300 µL resin were mixed by the batch method. The collected resin was eluted with 1 mL TE, 1 mL 400 mM NaCl in TE. Four different resin/columns were then eluted with either 1 M NaCl in TE, buffer from the Qiagen nucleotide removal kit (PN buffer, solubilization buffer), buffer from the Qiagen Viral kit (AVL buffer, solubilization buffer) or 3.0 M GuSCN. The eluted solutions were each then processed by glycogen isopropanol co-precipitation, Nucleotide removal protocol (Qiagen Manual), viral RNA isolation protocol (Qiagen Manual), or Promega Wizard protocol, respectively. Using 1 mL urine equivalence per polymerase reaction, the presence of template was determined as described in Example 1, Section D, using the β-Actin primers and a Fam labeled TaqMan probe. The same samples were also analyzed for their effect on spiked Lambda DNA amplification with primers (Lmd f, Lmd r) and Hex (Lmg Hex) probe. The following Lambda primers (SEQ ID NOS 4-6, respectively, in order of appearance) were used:

```
Lambda Primers:
Lmd_f          5'-ACTTTATGAAAACCCACGTTGAGC-3'

Lmd_r          5'-CCAGAAGCCACGCCCATTAG-3'

Lmg Hex probe  5'-TGGGTAATGCGCGGGTTGTCCTTT-3'
```

Calibration curves were generated using human standard and lambda phage genomic DNA and are summarized in Tables 2 and 3.

TABLE 2

| Urine ($A_{260}$) | Resin | Elution (1 mL) | β-Actin Ct | ng/rxn | Lambda Ct | ng/rxn |
|---|---|---|---|---|---|---|
| 16 | Q | 1M NaCl | — | | — | |
| | | PN buffer | 25.3 | 3.04 | 25.7 | 1.37 |
| | | AVL buffer | 24.9 | 3.84 | 26.0 | 1.14 |
| | | Wizard buffer | 24.9 | 3.95 | 25.7 | 1.38 |
| 48 | Q | 1M NaCl | — | | — | |
| | | PN buffer | 23.9 | 7.20 | 25.1 | 2.17 |
| | | AVL buffer | 23.7 | 8.35 | 24.5 | 3.37 |
| | | Wizard buffer | 24.7 | 4.38 | 24.7 | 2.94 |

$A_{260}$ - UV absorbance of urine sample, Q Q-Sepharose ™- initial resin with batch process loading, PN - nucleotide removal Qiagen kit, AVL - Qiagen viral kit, Wizard - used 3 M GITC and 100 μL of silica slurry, 2 M GITC - next elution after 1 M NaCl.

TABLE 3

Genomic Standard DNA

| | ng/rxn | β-Actin Ct | Lambda Ct |
|---|---|---|---|
| Control TE (5 μL) | | — | 25.8 |
| 0.02 ng/μL | 0.12 | 30.5 | 26.1 |
| 0.23 ng/μL | 1.17 | 26.7 | 25.8 |
| 2.34 ng/μL | 11.7 | 23.2 | 25.8 |
| 0.23 ng/μL (5/12) | 1.17 | 23.8 | 26.4 |
| Control TE (5 μL) | | — | 25.1 |

Figure 6:
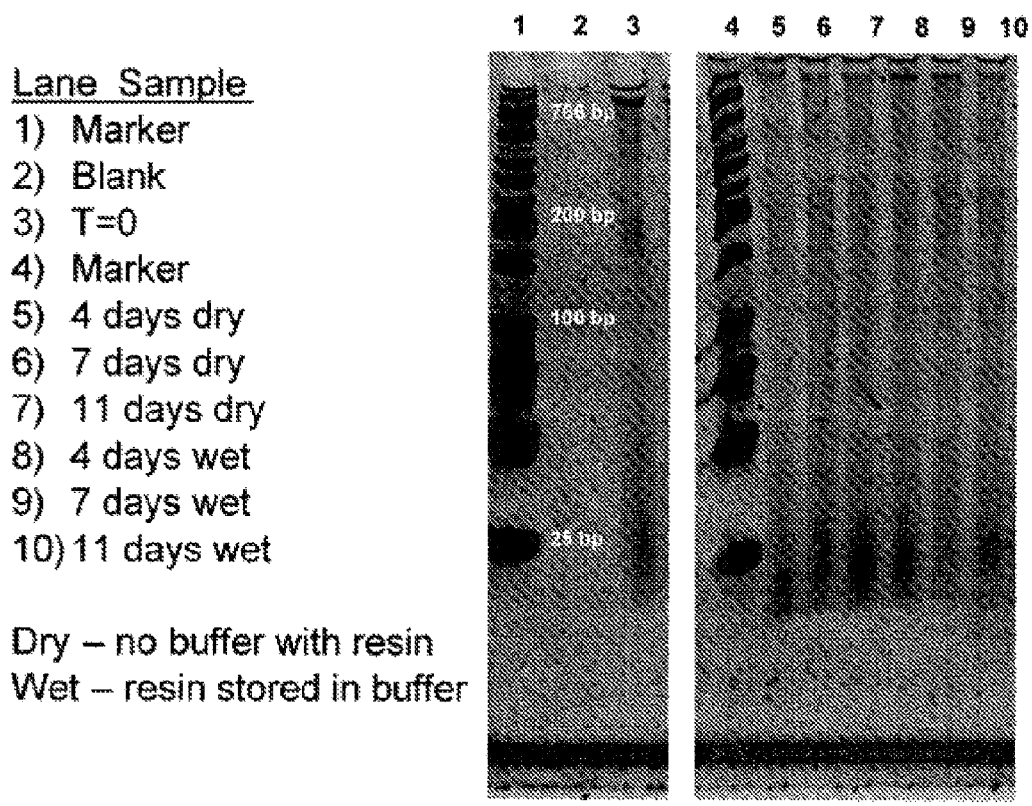
FIG. 6 is a photograph of a polyacrylamide gel showing stability of nucleic acids adsorbed onto Q-resin.

Comparison of Nucleic Acids Stability Stored on Wet and Dehydrated O-Resin:

Further experiments determining stability of the nucleic acids bound to Q Sepharose were performed. For these experiments, unfiltered urine (10 mL) and 150 μL Q-Sepharose™ resin were mixed by the batch method. The resin was washed with 1 mL TE, 1 mL 400 mM NaCl in TE and finally 1 mL TE. The resin was either let air dry at room temperature, or capped with extra TE. At given time points, the resin was re-hydrated with 1 mL TE, and eluted with 1 M NaCl in TE. This was precipitated with glycogen and isopropanol, of which 2 mL urine equivalence was loaded onto the gel. As shown in FIG. 6, the mixture of nucleic acids and proteins remain unchanged for 11 days when bound to the Q-Sepharose™ resin, whether dried (lanes 5-7) or in buffer solution (lanes 8-10).

Figure 7:
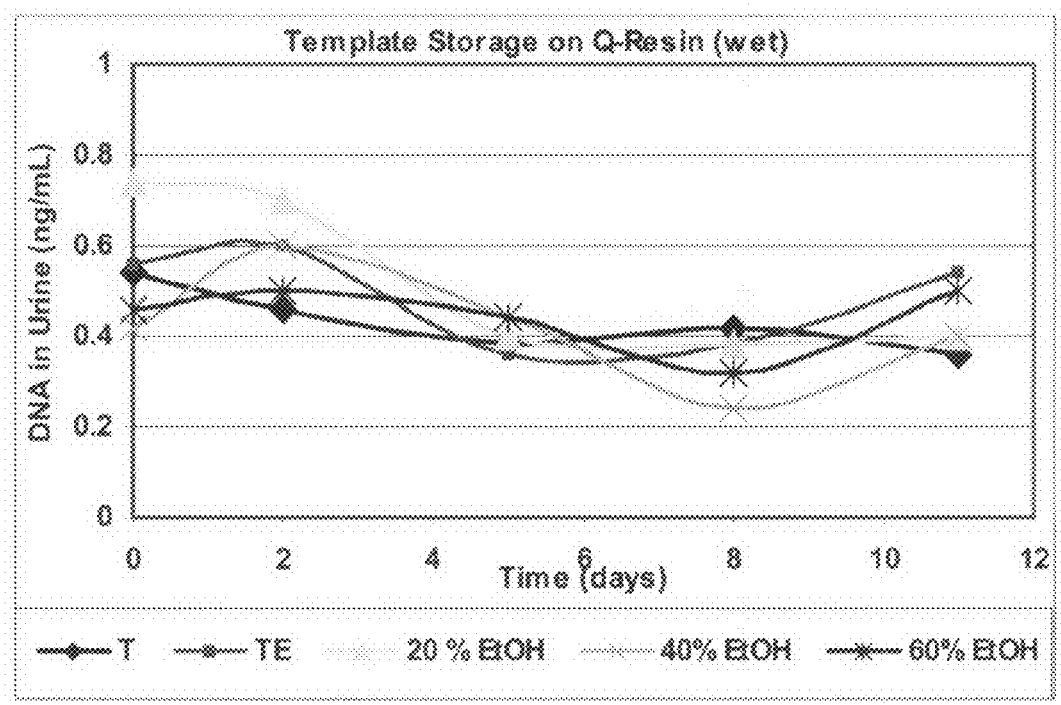
FIG. 7 is a photograph of graphical illustration of the stability of isolated DNA adsorbed on resin.

Further, experiments were conducted to examine, by real time PCR the stability of nucleic acid templates stored as a nucleoprotein/Q resin complexes. Similarly, FIG. 7 illustrates that nucleic acid templates remain stable over the course of 11 days. The results of these experiments clearly indicate that after adsorption and storage on Q-Sepharose™ the nucleic acids remain stable (Table 4).

TABLE 4

| Resin | Storage buffer | Days | Ct | ng/rxn |
|---|---|---|---|---|
| Q | T | 0 | 28.1 | 0.27 |
| | TE | 0 | 28.1 | 0.28 |
| | 20% EtOH | 0 | 27.5 | 0.37 |
| | 40% EtOH | 0 | 28.6 | 0.21 |
| | 60% EtOH | 0 | 28.4 | 0.23 |
| Q | T | 2 | 28.4 | 0.23 |
| | TE | 2 | 27.9 | 0.30 |
| | 20% EtOH | 2 | 27.7 | 0.35 |
| | 40% EtOH | 2 | 27.9 | 0.30 |
| | 60% EtOH | 2 | 28.2 | 0.25 |
| Q | T | 5 | 28.7 | 0.19 |
| | TE | 5 | 28.9 | 0.18 |
| | 20% EtOH | 5 | 28.6 | 0.20 |
| | 40% EtOH | 5 | 28.5 | 0.22 |
| | 60% EtOH | 5 | 28.5 | 0.22 |
| Q | T | 8 | 28.5 | 0.21 |
| | TE | 8 | 28.7 | 0.19 |
| | 20% EtOH | 8 | 28.7 | 0.19 |
| | 40% EtOH | 8 | 29.5 | 0.12 |
| | 60% EtOH | 8 | 29.1 | 0.16 |
| Q | T | 11 | 28.8 | 0.18 |
| | TE | 11 | 28.1 | 0.27 |
| | 20% EtOH | 11 | 28.7 | 0.20 |
| | 40% EtOH | 11 | 28.6 | 0.20 |
| | 60% EtOH | 11 | 28.2 | 0.25 |

H) Batch vs. Column vs. Vacuum

Experiments were conducted to demonstrate that the loading rate of urine sample onto Q-Sepharose™ has minimal effect on the binding of the various components. For these experiments, urine (20 mL) was loaded onto four different resins (400 μL) in four different modes:

1. By batch as described above, mixing resin and urine sample for 40 minutes.

2. By fast contact (under a minute with a Q-Sepharose™ packed Mini Columns: (Columns available from BioRad: 5 cm Bio-Spin 732-6008 or 3 cm Micro BioSpin 732-6204; or from Sigma C2728-200 or equivalent column with 30 um pore size frit).

3. By slow contact (about 8 minutes) with a Q-Sepharose™ packed Mini Columns. The columns were eluted at 2,500 rpm (1303 g) for 5 minutes using a Sorvall TR-5 centrifuge (Newtown, Conn.), RTH-250 with a swing bucket rotor, by syringe through a resin packed column cartridge (3 to 6 minutes), or 4. By using a vacuum manifold on a Q-Sepharose™ resin packed cartridge with a luer lock fitting.

Figure 8:
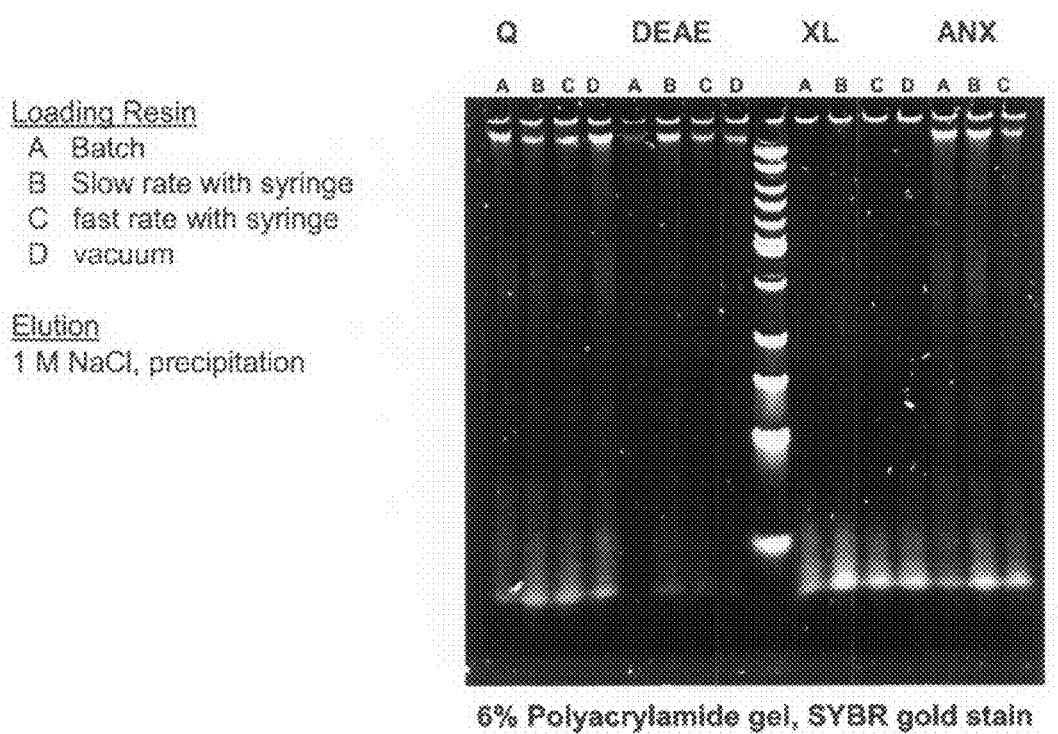
FIG. 8 is a photograph of a polyacrylamide gel comparing different loading rates, such as batch, column and vacuum, on isolating nucleic acids from urine.

After loading in each case, the resin was rinsed with 400 mM NaCl and eluted with 1 M NaCl in TE. The nucleic acids were precipitated with carrier, e.g. glycogen and isopropanol. Each lane contains 4 mL urine equivalence. As shown in Table 5 and FIG. 8, there were no differences on Q-Sepharose adsorption of the nucleic acids regardless of the loading method.

An analysis with PCR shows similar retention of template for all samples measured. The data is summarized in Table 5.

TABLE 5

| Resin | Flow Method | Time | Ct |
|---|---|---|---|
| Q-Sepharose ™ | Batch | 40:00 | 24.4 |
| | Slow | 8:20 | 25.1 |
| | Fast | 0:45 | 25.1 |
| | Vacuum | 6:02 | 24.8 |
| DEAE-Sepharose | Batch | 40:00 | 26.7 |
| | Slow | 8:13 | 25.8 |
| | Fast | 0:54 | 25.9 |
| | Vacuum | 3:36 | 25.7 |
| XL-Sepharose | Batch | 40:00 | 41.2 |
| | Slow | 8:37 | not applicable |
| | Fast | 0:55 | 39.0 |
| | Vacuum | 4:37 | 27.8 |
| ANX-4-Sepharose | Batch | 40:00 | 24.6 |
| | Slow | 8:30 | 24.8 |
| | Fast | 0:54 | 25.2 |

Figure 9:
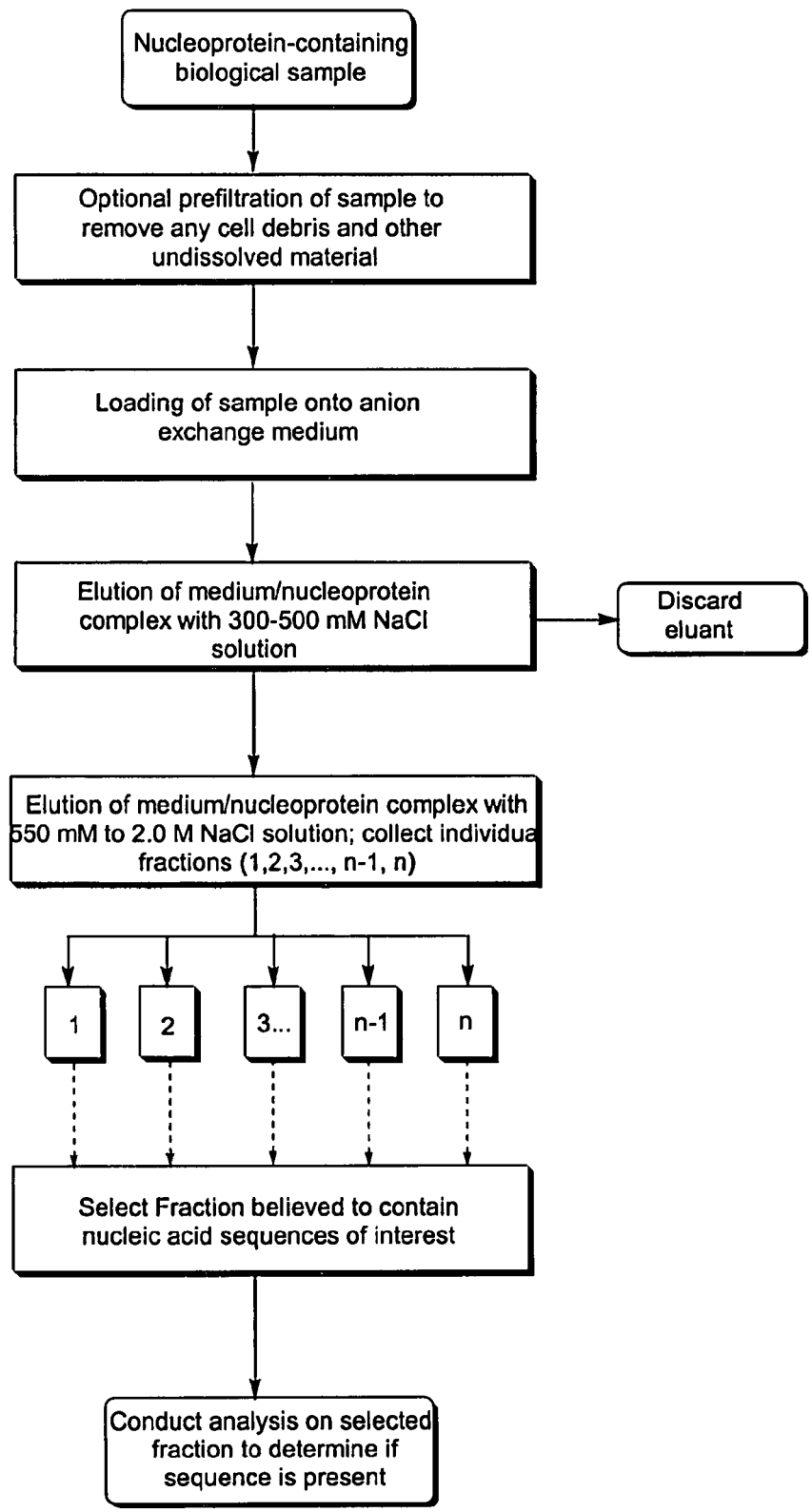
FIG. 9 is a Flow Diagram summarizing the general purification and concentration procedure.
Figure 10:
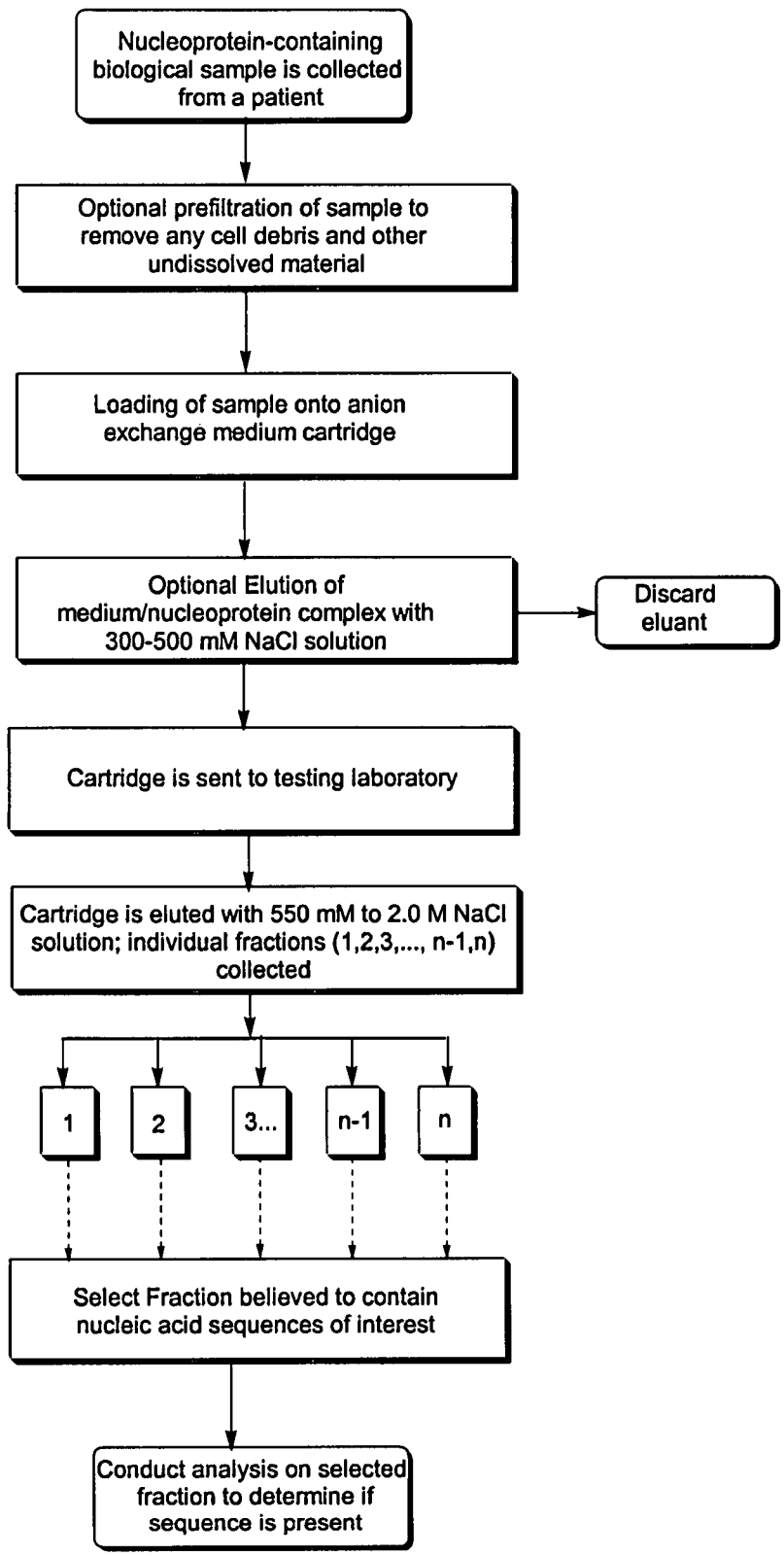
FIG. 10 is a Flow Diagram summarizing a purification and concentration procedure using a cartridge which is then used for storage, stabilization and transport of the sample.

The instant method of isolation of nucleic acids from urine is summarized graphically in FIGS. 9 and 10.

Example 2

Plasma Preparation

For these experiments, blood samples from healthy donors were collected in BD VACUTAINER Venous Blood Collection tubes containing anticoagulant EDTA (K3). Blood cells were removed by 10 min centrifugation at 1,000 rpm.

Isolation of Nucleic Acids Contained in Blood Plasma

Protocol 1 (DNA Isolation).

The plasma sample was supplemented with an equal volume of 0.4 M NaCl solution prepared on TE. Twenty milliliters of diluted plasma were mixed with 0.5 ml of Q-resin slurry and incubated 15 to 60 min at room temperature. Then the mixture was centrifuged for 5 min at 1900×g and the pelleted resin was transferred into a minicolumn (Bio-Rad). Before elution with 1.0 M NaCl the resin was washed two times with 0.5 M NaCl. The eluted nucleic acids were precipitated by addition of an equal volume of 100% isopropanol using glycogen as a carrier and re-suspended in 100 µL TE (10 mM Tris buffer and 1 mM EDTA).

Protocol 2 (DNA and RNA Isolation)

Preparation of plasma for Q-binding: 1 mL of a plasma sample from a healthy volunteer was supplemented with EDTA and Tris-HCl buffer (pH 8.0) to the final concentrations of 50 mM and digested with 75 µl Proteinase K (Qiagen) for 1 hour at 37° C. After the digestion the volume of mixtures was brought to 5 mL by adding 4 mL of a solution containing 50 mM EDTA; 50 mM Tris-HCl (pH 8.0) and 0.01% Tween 20.

Q Binding: The diluted plasma samples were allowed to bind in batch mode for 10 min to 250 µl of unwashed Q-Sepharose™ (GE Healthcare) in a 15 mL centrifuge tubes at room temperature. The resin was collected by centrifugation at 2,000×g for 5 min at room temperature in a table top clinical centrifuge using a swing bucket rotor. All but about 0.5 mL of supernatant was removed by aspiration. The resin pellet was resuspended in the remaining supernatant and transferred to a Micro Bio-Spin Chromatography Column (Bio-Rad). The resin was collected by pulse centrifugation in a microfuge for ~10 sec (~10 k RPM) and the flow-through liquid was discarded. The column was washed three times with 500 µl of 300 mM LiCl/10 mM NaOAc (pH 5.2).

Elution of Q-Sepharose™ bound nucleic acids: The bound nucleic acids were collected by two consecutive 200 µl elution with either 2 M LiCl/10 mM NaOAc (pH 5.2) Purified nucleic acids were desalted by adsorption on silica as described above.

Protocol 3 (RNA Isolation)

Preparation of plasma for Q-binding: 1 mL plasma sample from a healthy volunteer was supplemented with EDTA and Tris-HCl buffer (pH 8.0) to the final concentrations of 50 mM and with 40 µl RNAse inhibitor—RNAsecure (Ambion). The mixture was heated 10 min at 60° C. to inactivate ribonucleases present in plasma. For digestion of plasma proteins 75 µl Proteinase K (Qiagen) was added to the mixture and incubated 1 hour at 37° C. After the digestion the volume of mixtures was brought to 5 mL by adding 4 mL of a solution containing 50 mM EDTA; 50 mM Tris-HCl (pH 8.0) and 0.01% Tween 20.

Q Binding: The diluted plasma sample was allowed to bind in a batch mode for 10 min to 250 µl of unwashed Q-Sepharose™ (GE Healthcare) in a 15 mL centrifuge tubes at room temperature. The resin was collected by centrifugation at 2,000×g for 5 min at room temperature in a table top clinical centrifuge using a swing bucket rotor. All but about 0.5 mL of supernatant was removed by aspiration. The resin pellets were resuspended in the remaining supernatants and transferred to a Micro Bio-Spin Chromatography Column (Bio-Rad). The resin (~65 µl packed volume) was collected by pulse centrifugation in a microfuge for ~10 sec (~10,000 rpm) and the flow-through liquid was discarded. The column was washed three times with 500 µl of 300 mM LiCl/10 mM NaOAc (pH 5.2).

Elution of Q-Sepharose™ bound nucleic acids: The bound nucleic acids were collected by two consecutive elution with 200 µl of either 2 M LiCl/10 mM NaOAc (pH 5.2) or TRIzol™ reagent (Invitrogen).

TRIzol™ Phase Separation: The two 200 µl TRIzol eluates from each column were pooled and supplemented with 80 µl of CHCl$_3$/isoamyl alcohol (24:1). The samples were shaken by hand and following 3 min room temperature incubation were centrifuged at 12,000×g for 15 min at 4° C. 240 µl of the upper aqueous phase from each tube was transferred to fresh tubes.

Precipitation of TRIzol™ eluted nucleic acids: The nucleic acids from the upper aqueous phase were precipitated at −20° C. for 30 min by the addition of 1 µl of 20 mg/mL glycogen (Roche) and 240 µl of 100% isopropyl alcohol. The precipitate was collected by centrifugation and washed twice with 200 µl of 70% ethanol. The pellet was dried for 5 min at room temperature and then resuspended in 30 µl of 0.1 mM EDTA/ 1×RNA Secure (Ambion). The sample was incubated at 60° C. for 10 min to inactivate any residual RNase or DNAse activity.

Figure 12:
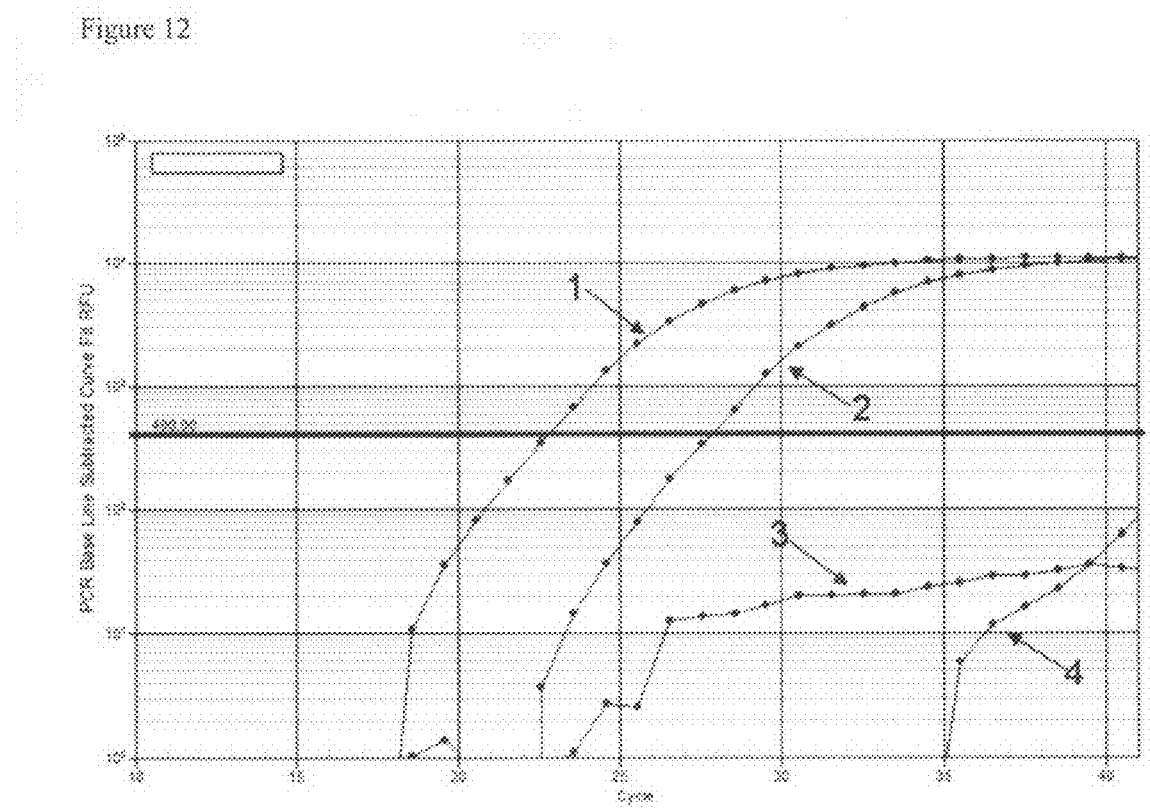
FIG. 12 is real time PCR graph showing the presence of micro RNA 16 (mir-16) in TRYzol eluted nucleic acids from blood plasma.

Silica based purification of eluted nucleic acids was performed as described above. Analysis of nucleic acids purified from plasma: TRIzol eluted plasma nucleic acid preparation was subjected to further analysis. We have chosen abundantly expressed microRNA 16 (mir-16) as a target. Five µL aliquots of each sample of TRIzol purified plasma nucleic acids were subjected to TaqMan microRNA quantitative PCR reaction using primers and probe supplied from Applied Biosystem. Reactions were carried out essentially as per manufacturer's recommendations. Mir-16 was easily detectable in plasma RNA preparation. The results of these experiments were summarized in FIG. 12.

What is claimed is:

1. A method of isolating cell-free nucleic acids from a sample of urine comprising:

a) obtaining a cell containing urine sample from a subject and separating said sample into a cell-free fraction, containing nucleic acids in the size range of 10 to 100 base pairs, and a cell-containing fraction by filtration or centrifugation;

b) selecting an anion exchange material comprising quaternary ammonium groups and which effectively adsorbs target nucleic acids or proteinous complexes thereof present within said cell-free fraction;

c) applying said cell-free fraction of said urine sample containing nucleic acids or their proteinous complexes to the selected anion exchange material, and said nucleic acids or their complexes adsorb to said material to form bound target nucleic acids or their complexes;

d) optionally washing said anion exchange material with an aqueous solution of a salt at which the target nucleic acids or their complexes remain bound to said anion exchange material, said washing being of sufficient volume and ionic strength to wash the non-binding or weakly binding components through said anion exchange material;

e) eluting the said bound target nucleic acids or their complexes by passing through said anion exchange material an aqueous solution of increasing ionic strength to remove in succession proteins that are not bound or are weakly bound to the anion exchange material and said nucleic acids of increasing molecular weight from said material; and f) isolating the eluted nucleic acid fraction containing nucleic acids in the size range of 10 to 100 base pairs.

2. The method of claim 1, wherein said nucleic acids are selected from the group consisting of double- and single-stranded DNA and RNA.

3. The method of claim 1, further comprising the step of maintaining the bound target nucleic acids or their complexes in storage for up to 3 weeks prior to elution and isolation of said nucleic acid.

4. A method of isolating cell-free nucleic acids from a sample of blood plasma comprising:

a) obtaining a cell containing blood sample from a subject and separating said sample into a cell-free fraction, containing nucleic acids in the size range of 10 to 100 base pairs, and a cell-containing fraction by filtration or centrifugation;

b) selecting an anion exchange material which effectively adsorbs target nucleic acids or proteinous complexes thereof present within said cell-free fraction;

c) applying said cell-free fraction of said blood plasma sample containing nucleic acids or their proteinous complexes to the selected anion exchange material, and said nucleic acids or their complexes adsorb to said material to form bound target nucleic acids or their complexes;

d) optionally washing said anion exchange material with an aqueous solution of a salt at which the target nucleic acids or their complexes remain bound to said anion exchange material, said washing being of sufficient volume and ionic strength to wash the non-binding or weakly binding components through said anion exchange material;

e) eluting the said bound target nucleic acids or their complexes by passing through said anion exchange material an aqueous solution of increasing ionic strength to remove in succession proteins that are not bound or are weakly bound to the anion exchange material and said nucleic acids of increasing molecular weight from said material; and f) isolating the eluted nucleic acid fraction containing nucleic acids in the size range of 10 to 100 base pairs.

5. The method of claim 4, wherein said nucleic acids are selected from the group consisting of double- and single-stranded DNA and RNA.

6. The method of claim 4, further comprising the step of maintaining the bound target nucleic acids or their complexes in storage for up to 3 weeks prior to elution and isolation of said nucleic acid.

7. The method of claim 4, wherein said anion exchange material is selected from the group consisting of tertiary and quaternary ammonium groups.

8. A method of isolating cell-free nucleic acids from a sample of urine comprising:

a) separating a cell-free fraction, containing nucleic acids in the size range of 10 to 100 base pairs, apart from cells present in a urine sample from a subject and;

b) selecting an anion exchange material comprising quaternary ammonium groups, which material effectively adsorbs target nucleic acids or proteinous complexes thereof present within said cell-free fraction;

c) applying said cell-free fraction, containing nucleic acids or their proteinous complexes, to the selected anion exchange material, and said nucleic acids or their complexes adsorb to said material to form bound target nucleic acids or their complexes;

d) optionally washing said anion exchange material with an aqueous solution of a salt at which the target nucleic acids or their complexes remain bound to said anion exchange material, said washing being of sufficient volume and ionic strength to wash the non-binding or weakly binding components through said anion exchange material;

e) eluting the said bound target nucleic acids or their complexes by passing through said anion exchange material an aqueous solution of increasing ionic strength to remove in succession proteins that are not bound or are weakly bound to the anion exchange material and said nucleic acids of increasing molecular weight from said material; and f) isolating the eluted nucleic acid fraction containing nucleic acids in the size range of 10 to 100 base pairs.

9. The method of claim 8, wherein said separating a cell-free fraction is by filtration or centrifugation.

10. The method of claim 8, wherein said nucleic acids are selected from the group consisting of double- and single-stranded DNA and RNA.

11. The method of claim 8, further comprising the step of maintaining the bound target nucleic acids or their complexes in storage for up to 3 weeks prior to elution and isolation of said nucleic acid.

* * * * *